(12) United States Patent
Nakayama et al.

(10) Patent No.: US 7,848,482 B2
(45) Date of Patent: Dec. 7, 2010

(54) X-RAY CT DEVICE AND METHOD OF MANUFACTURING THE SAME

(75) Inventors: Tadahiro Nakayama, Yokohama (JP); Masato Nagata, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 12/266,925

(22) Filed: Nov. 7, 2008

(65) Prior Publication Data
US 2009/0116618 A1 May 7, 2009

(30) Foreign Application Priority Data
Nov. 7, 2007 (JP) .............................. 2007-289887
Oct. 24, 2008 (JP) .............................. 2008-274281

(51) Int. Cl.
*H05G 1/10* (2006.01)
(52) U.S. Cl. .............................. 378/15; 378/4; 378/101
(58) Field of Classification Search .................. 378/4, 378/15, 19, 101; 336/120
See application file for complete search history.

(56) References Cited

U.S. PATENT DOCUMENTS

| | | | | |
|---|---|---|---|---|
| 4,912,735 | A * | 3/1990 | Beer | 378/15 |
| 5,272,612 | A * | 12/1993 | Harada et al. | 363/8 |
| 5,572,178 | A * | 11/1996 | Becker et al. | 336/120 |
| 5,608,771 | A * | 3/1997 | Steigerwald et al. | 378/15 |
| 6,674,836 | B2 * | 1/2004 | Harada et al. | 378/107 |
| 7,054,411 | B2 * | 5/2006 | Katcha et al. | 378/101 |
| 7,197,113 | B1 * | 3/2007 | Katcha et al. | 378/101 |
| 7,375,993 | B2 * | 5/2008 | Beland | 363/71 |
| 7,400,708 | B2 * | 7/2008 | Takahashi et al. | 378/109 |
| 7,634,046 | B2 * | 12/2009 | Krumme | 378/19 |
| 2006/0022785 | A1 * | 2/2006 | Dobbs | 336/120 |

FOREIGN PATENT DOCUMENTS

JP   3827335 B2   7/2006

* cited by examiner

*Primary Examiner*—Edward J Glick
*Assistant Examiner*—Thomas R Artman
(74) *Attorney, Agent, or Firm*—Pillsbury Winthrop Shaw Pittman LLP

(57) ABSTRACT

An X-ray CT device, including a stationary part; a rotary part; an X-ray tube provided at the rotary part and that radiates X-ray beams on an object of imaging; an X-ray detector being provided at the rotary part and that detects the X-ray beams; an image processor that generates cross-sectional images of the object; a display that shows the cross-sectional images; a rotary step-up transformer that steps up AC voltage and including a primary and secondary part, the primary part being annular and being provided at the stationary part and including a primary winding being provided circumferentially and the secondary part being provided at the rotary part so as to confront the primary part over a gap and including a plurality of secondary cores disposed circumferentially and a secondary winding being wound on each of the secondary cores and being interconnected in series.

19 Claims, 16 Drawing Sheets

X-RAY CT DEVICE AND METHOD OF MANUFACTURING THE SAME

CROSS-REFERENCE TO RELATED APPLICATIONS

This application is based upon and claims the benefit of priority from the prior Japanese Patent Applications 2007-289887, filed on, Nov. 7, 2007, and 2008-274281, filed on, Oct. 24, 2008 the entire contents of which are incorporated herein by reference.

FIELD

The present disclosure relates to an X-ray CT device provided with a stationary part and a rotary part configured rotatably relative to the stationary part. Power is supplied to an X-ray tube provided at the rotary part from the stationary part. The present disclosure also relates to a method of manufacturing the X-ray CT device.

BACKGROUND

An X-ray CT (Computed Tomography) device is known for generating cross-sectional images of an object. More specifically, a cross-sectional image is generated by producing X-ray beams with an X-ray tube, which is passed through the object and converting the transmitted X-ray into signals that provide basis for generating a cross-sectional image of the object. To produce such image, X-ray CT device is typically arranged to rotate a rotary part, including the X-ray tube and the X-ray detector, relative to a stationary part. Conventionally, in order to transmit power to the rotary part from the stationary part, a slip ring-brush configuration has been employed. However, the slip ring-brush configuration, requiring contact between the components, requires tedious maintenance work to recover component wear-out.

In view of the above concerns, JP 3827335 B discloses an electromagnetic induction transformer comprising a primary side and a secondary side, the primary side being provided at the stationary part and the secondary side being provided at the rotary part. The stationary part converts AC (Alternate Current) voltage provided by commercially available AC power into high-frequency voltage with a DC (Direct Current) power circuit and an inverter circuit. The high-frequency voltage is applied on the primary side. The rotary part, on the other hand, utilizes a high-voltage transformer for further stepping up the high-frequency voltage generated at the secondary side to a required voltage level to be supplied to the X-ray tube. The stepped up high-frequency voltage is rectified by the rectifier circuit, and the rectified DC voltage is applied to the X-ray tube. According to the above described configuration, burden of maintenance checkup for providing non-contact power transmission from the stationary part to the rotary part can be reduced.

The X-ray tube, however, requires application of high voltages ranging from 70 kV to 150 kV. The high-voltage transformer according to the conventional configuration needs to be increased in size in order to provide relatively higher voltages, which in turn leads to increased weight that may amount to 100 kg, for example. Such heavy and sizable high-voltage transformer, when provided at the rotary part, imparts increased centrifugal force upon rotation of the rotary part. Increased centrifugal force consequently requires structural reinforcement of the rotary part which in turn unwantedly causes increase in weight, leaving the problem of increased centrifugal force unsolved. Thus, one may conceive to reduce the maximum rotational speed in order to reduce the centrifugal force. However, maximum rotational speed of the rotary part is a critical factor in determining the quality of images generated by the X-ray CT device, such that when reduced, does not provide improved imaging quality.

Further, when heavy and sizable components are provided at the rotary part, balance of weight of the rotary part becomes unstabilized and may cause unwanted rotational variance. Rotational variance may be restrained by placing a balancer at the rotary part. However this will further increase the weight of the rotary part, which in turn increases the centrifugal force.

SUMMARY

The present disclosure provides an X-ray CT device that allows power to be supplied to an X-ray tube provided at a rotary part from a stationary part by non-contact power transmission. The present disclosure also provides a method of manufacturing the X-ray CT device.

In one aspect, an X-ray CT device of the present disclosure includes a stationary part; a rotary part provided rotatably relative to the stationary part; an X-ray tube being provided at the rotary part and that radiates X-ray beams on an object of imaging; an X-ray detector being provided at the rotary part so as to oppose the X-ray tube, and that detects the X-ray beams passed through the object; an image processor that generates cross-sectional images of predetermined portions of the object based on a detection signal outputted from the X-ray detector; a display that shows the cross-sectional images based on output signals delivered from the image processor; a rotary step-up transformer that steps up AC voltage provided by AC power supply, the rotary step-up transformer including a primary part and a secondary part, the primary part being annular in form and being provided at the stationary part and including a primary winding being provided circumferentially, and the secondary part being provided at the rotary part so as to confront the primary part over a gap and including a plurality of secondary cores disposed circumferentially and a secondary winding being wound on each of the secondary cores and being interconnected in series.

According to the above described configuration, since AC voltage provided by AC power source need not be stepped up at the rotary part, heavy-weight components dedicated for voltage step-up need not be provided at the rotary part. Thus, non-contact power transmission can be executed from the stationary part to the rotary part for supplying power to the X-ray tube with lighter rotary part. Moreover, stepped-up high voltage generated at the secondary side of the rotary step-up transformer can be configured by increasingly compact insulation since secondary winding is wound on each of the secondary cores.

BRIEF DESCRIPTION OF THE DRAWINGS

Other objects, features and advantages of the present disclosure will become clear upon reviewing the following description of the exemplary embodiments with reference to the accompanying drawings, in which, FIG. 1 indicates an electric configuration of an X-ray CT device according to a first exemplary embodiment of the present disclosure.

DETAILED DESCRIPTION

A first exemplary embodiment of the present disclosure will be described with reference to FIGS. 1 to 13.

Figure 1:
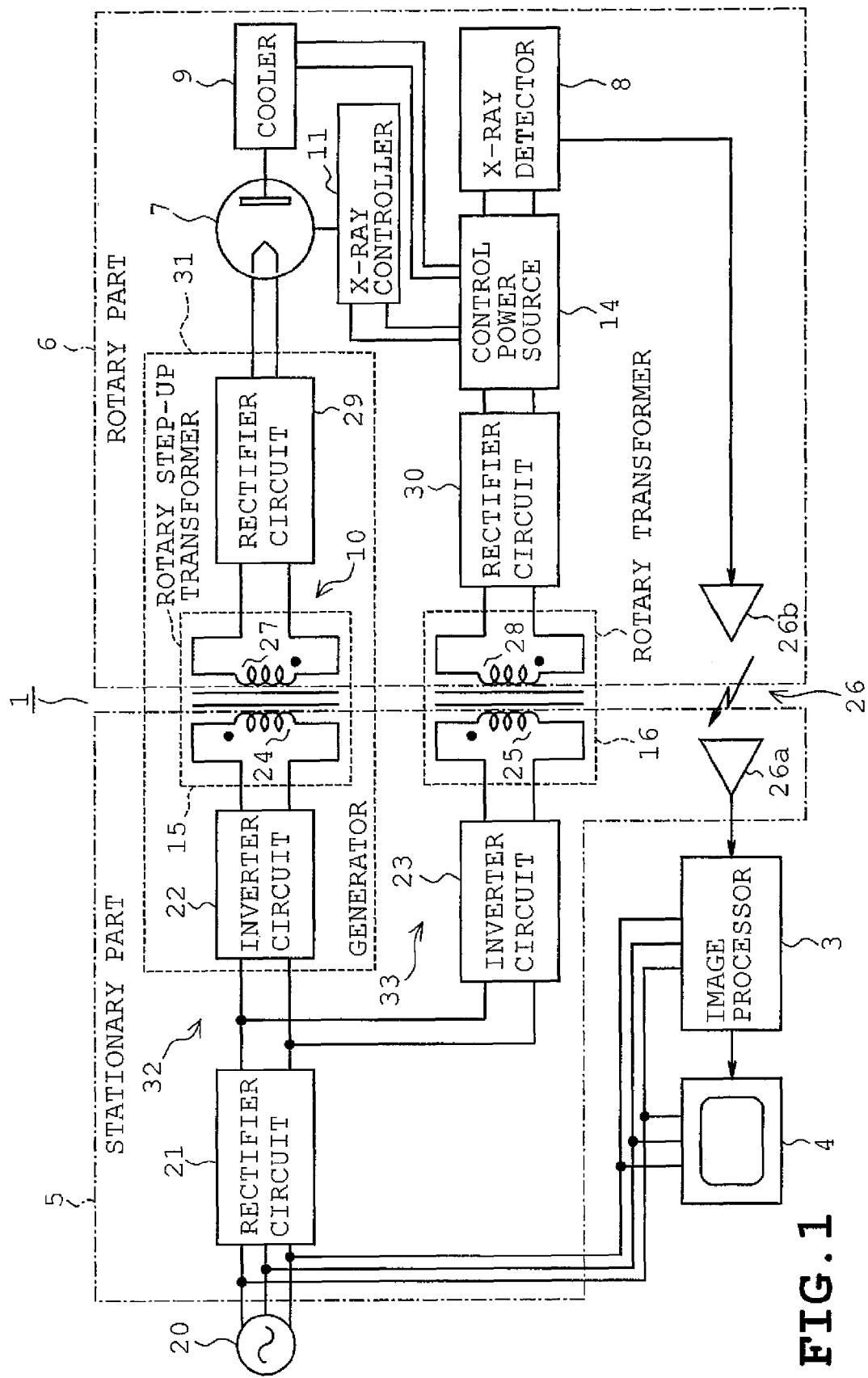
Figure 2:
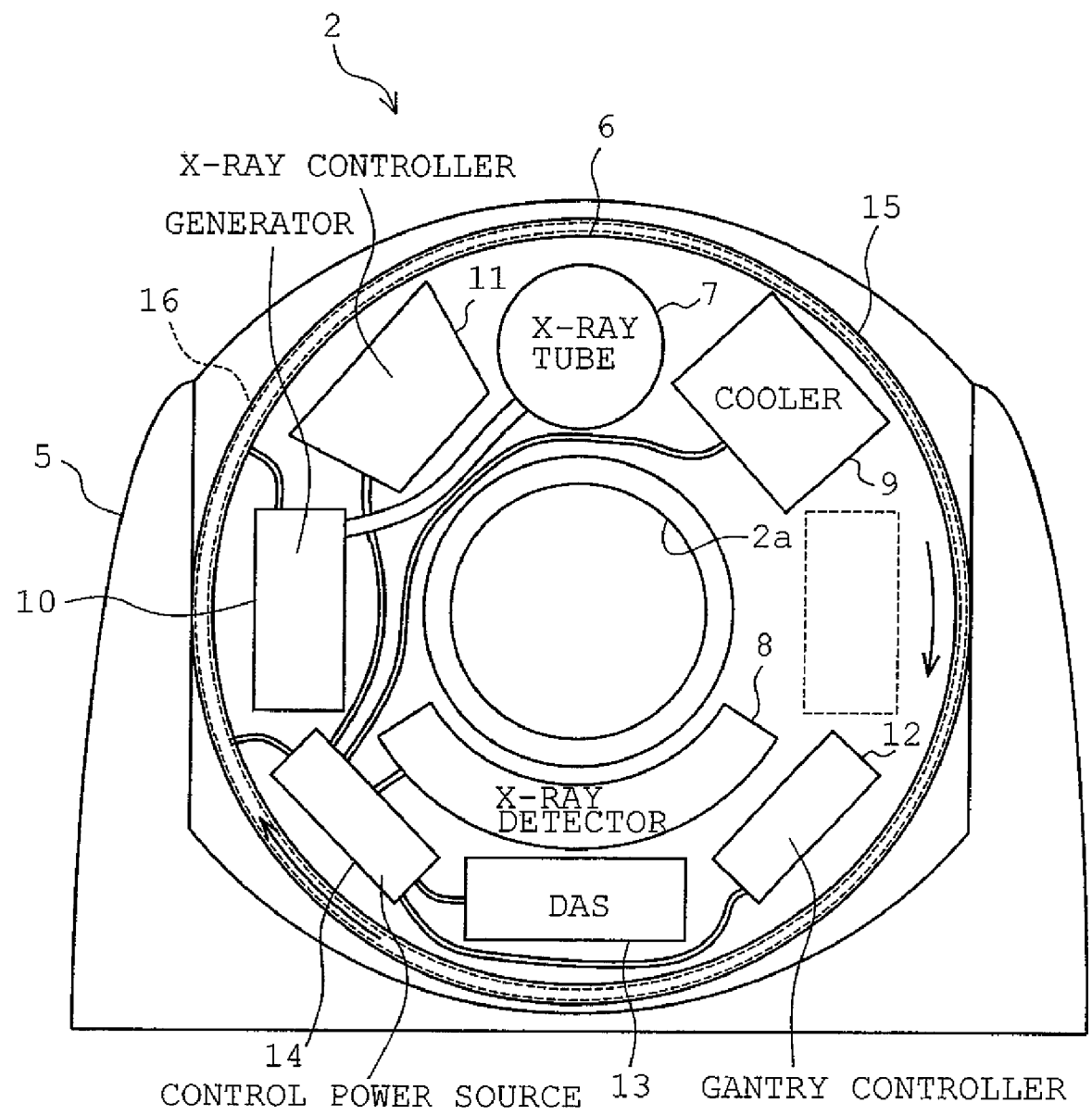
FIG. 2 is cross-sectional front view providing a look of a gantry and a part of its interior configuration.

Referring to FIGS. 1 and 2, an X-ray CT (computerized tomography) device 1 includes a gantry 2, an image processor 3, a display 4, and a bed (not shown). Gantry 2 radiates X-ray beams on an object from the periphery of the object. Gantry 2 also detects X-ray beams passed through the object. Image processor 3 generates cross-sectional image of the object based on the data detected from the transmitted X-ray beam. The generated cross-sectional image is shown on display 4. The bed receives and guides the object to gantry 2.

FIG. 2 is a cross-sectional front view depicting the exterior and schematic configuration of gantry 2 provided at X-ray CT device 1. As shown in FIG. 2, gantry 2 has an opening 2a formed as a cylindrical through hole defined substantially at its center. The bed carrying the object is passed through opening 2a to produce X-ray CT images. Gantry 2 comprises a stationary part 5 defining its exterior housing and a rotary part 6 rotatably supported by stationary part 5. Rotary part 6 is rotated about opening 2a by a drive circuit and motor not shown.

Provided inside rotary part 6 are an X-ray tube 7 that produces X-ray beams and an X-ray detector 8 that detects X-ray beams passed through the object. X-ray tube 7 and X-ray detector 8 confront each other over opening 2a. X-ray detector 8 detects X-ray beams radiated from X-ray tube 7 and passed through the object. Further provided inside rotary part 6 are a cooler 9 for cooling X-ray tube 7, a generator 10 for supplying high voltage to X-ray tube 7, an X-ray controller 11, a gantry controller 12, a DAS 13, and a control power source 14. X-ray controller 11 controls output of X-ray tube 7 through control of generator 10 depending on preset settings.

X-ray controller 11 is capable of detecting abnormalities occurring at X-rat tube 7. When detecting such abnormalities, X-ray controller 11 stops power supply to X-ray tube 7. One exemplary approach for detecting abnormalities of X-ray tube 7 is a comparative approach in which actual amount of current and voltage provided to X-ray tube 7 is compared with a predetermined reference current and reference voltage. Gantry controller 12 controls components such as cooler 9 provided at rotary part 6. DAS (Data Acquisition System) 13 converts output (current signal) of X-ray detector 8 into digital data allowing processing with a computer. Control power source 14 supplies power to each component provided at rotary part 6 exclusive of X-ray tube 7.

Referring to FIG. 2, the area surrounded by a broken line indicates the portion where a heavy and sizable high-voltage transformer was conventionally provided. FIG. 2 merely schematically explains the availability of such space inside rotary part 6 of the present exemplary embodiment and does not precisely specify the positioning of each component thought it does properly indicate the relative positioning of X-ray tube 7 and X-ray detector 8. The components are positioned more elaborately in reality to balance the distribution of weight inside rotary part 6.

Rotary step-up transformer 15 and rotary transformer 16 being annular in form are provided to reside at both stationary part Sand rotary part 6. Rotary step-up transformer 15 and rotary transformer 16 have a primary side and a secondary side respectively. The primary sides of rotary step-up transformer 15 and rotary transformer 16 are provided at stationary part 5 respectively whereas the secondary sides are provided at rotary part 6, respectively as will be described in detail afterwards. Power is supplied to X-ray tube 7 through rotary step-up transformer 15 and generator 10 provided at rotary part 6. Power is supplied to X-ray detector 8, cooler 9, X-ray controller 11, gantry controller 12, and DAS 13 through components such as rotary transformer 16 and control power source 14. Rotary step-up transformer 15 and rotary transformer 16 execute non-contact power transmission from stationary part 5 to rotary part 6.

FIG. 1 is a block diagram indicating the electrical configuration of X-ray CT device 1. As can be seen in FIG. 1, stationary part 5 is provided with a rectifier circuit 21 that rectifies AC voltage supplied from AC power source 20, inverter circuits 22 and 23, primary winding 24 of rotary step-up transformer 15, primary winding 25 of rotary transformer 16, and a receiver 26a of a data transceiver 26. Rotary part 6, on the other hand, has secondary winding 27 of rotary step-up transformer 15, a secondary winding 28 of rotary transformer 16, rectifier circuits 29 and 30, X-ray tube 7, X-ray detector 8, cooler 9, control power source 14, and transmitter 26b of data transceiver 26. Inverter circuit 22, rotary step-up transformer 15, and rectifier circuit 29 described above constitute a generator 31. Generator 31 includes a generator 10 disposed at rotary part 6 as shown in FIG. 2, generator 10 comprising secondary side components of rotary step-up transformer 15 and rectifier circuit 29.

Turns ratio of primary winding 24 and secondary winding 27 of rotary step-up transformer 15 is set to provide a step-up ratio of "150" or greater. In other words, rotary step-up transformer 15 is configured so that voltage at the secondary side is at least 150 times greater than the primary side. Turns ratio of primary winding 25 and secondary winding 28 of rotary transformer 16 are set to provide a step-up ratio of "1". In other words, rotary transformer 16 is configured so that voltage at the secondary side and the primary side are equal.

Step-up ratio of rotary transformer 16 may be configured at any given ratio other than "1" as long as it is below the step-up ratio of rotary step-up transformer 15.

AC power source 20 is a commercial AC power source which produces an output of 415V (50 Hz/60 Hz) of three-phase Rectifier circuit 21 is configured by diodes in three-phase bridge connection. Rectifier circuit 21 has an AC input terminal that is connected to a power input terminal of X-ray CT device 1 which in turn is connected to AC power source 20. Rectifier circuit 21 further has a DC output terminal connected to input terminals of inverter circuits 22 and 23, respectively. Inverter circuits 22 and 23 convert DC voltage provided by rectifier circuit 21 into high-frequency voltage which is higher than the frequency (50 Hz/60 Hz) of commercial AC power source. High-frequency voltage outputted from inverter circuits 22 and 23 are applied to primary winding 24 of rotary step-up transformer 15 and primary winding 26 of rotary transformer 16, respectively.

In the present exemplary embodiment, rectifier circuit 21, inverter circuit 22 and rotary step-up transformer 15 constitute a first transmitting section 32 (corresponding to a transmitting section). First transmitting section 32 steps up AC voltage provided from AC power source 20 as well as enabling non-contact power transmission from stationary part 5 to rotary part 6 for power supply to X-ray tube 7. Rectifier circuit 21, inverter circuit 23, and rotary transformer 16 constitute a second transmitting section 33.

Data transceiver 26 performs non-contact data communication through medium such as light. Receiver 26a provided at stationary part 5 receives projection data transmitted from transmitter 26b provided at rotary part 6 to produce an output to image processor 3. Image processor configured primarily by a computer. Image processor 3 produces a cross-sectional view of the object based on the projection data provided by receiver 26a. Display 4 may comprise a liquid crystal display, for example, and receives input of data information representing cross-sectional images from image processor 3.

Image processor 3 and display 4 are each provided with a power source circuit (not shown) that converts three-phase AC voltage provided by AC power source 20 to their own operating voltages. Image processor 3 and display 4 operate with three-phase voltage supplied from AC power source 20. Power source may be supplied to image processor 3 and display 4 from external power source circuit.

Terminals at both ends of secondary winding 27 of rotary step-up transformer 15 are connected to AC input terminal of rectifier circuit 29. Rectifier circuit 29 is configured by bridge connected diodes. Rectifier circuit 29 rectifies high-frequency voltage generated at the terminals of secondary winding 27 to generate a DC voltage. DC voltage outputted from rectifier circuit 29 is applied to X-ray tube 7.

On the other hand, terminals at both ends of secondary winding 28 of rotary transformer 16 are connected to AC input terminal of rectifier circuit 30. Rectifier circuit 30 is configured by bridge connected diodes as in rectifier circuit 29. Rectifier circuit 30 has a DC output terminal connected to DC input terminal of control power source 14. Control power source 14 comprises a DC/DC converter that converts input DC voltage into the desired level of DC voltage. DC output of control power source 14 is provided to X-ray detector 8, cooler 9, and X-ray controller 11. Though not shown, DC output of control power source 14 is also provided to gantry controller 12 and DAS 13.

X-ray detector 8 outputs a detection signal (current signal) which is inputted into DAS 13 to be converted into digital data (projection data). DAS 13 transmits the projection data to receiver 26a provided at rotary part 5 through transmitter 26b of data transceiver 26 by optical communication.

Figure 3:
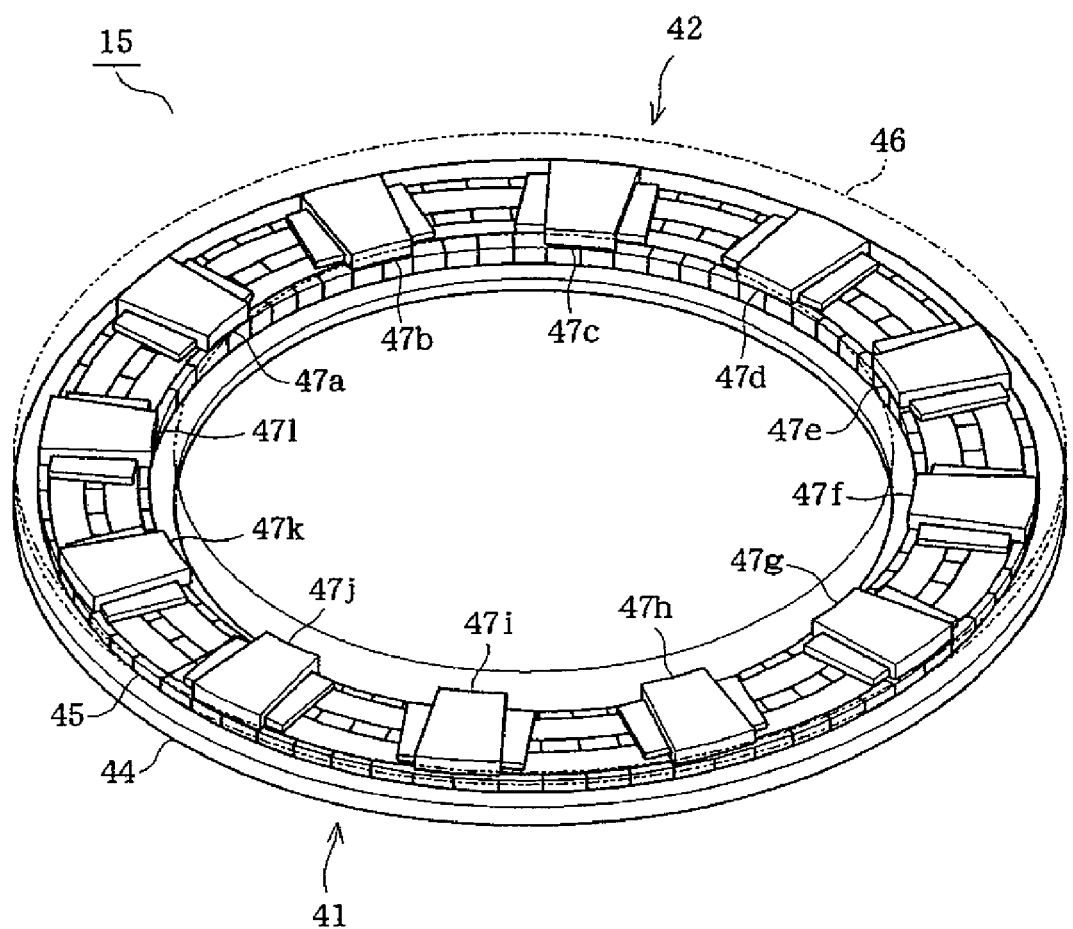
FIG. 3 is a schematic perspective view showing the entirety of a rotary step-up transformer.
Figure 4:
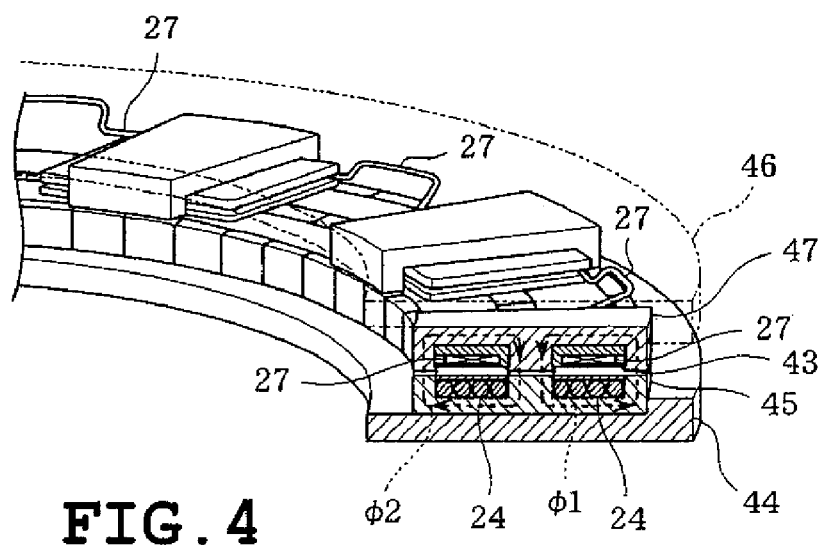
FIG. 4 is a perspective view depicting a circumferential cross-section of the rotary step-up transformer.

FIG. 3 is a perspective view showing the overall configuration of rotary step-up transformer 15. FIG. 4 is a partially enlarged view of FIG. 3, also showing a circumferential cross section of rotary step-up transformer 15. FIGS. 3 and 4 also provide a transparent image of a later described core holder 46 which is a component of rotary step-up transformer 15. A brief description will now be given on the configuration of rotary step-up transformer 15. Rotary step-up transformer 15 comprises a generally annular and concentric primary part 41 and a secondary part 42. Primary part 41 resides in stationary part 5 whereas secondary part 42 resides in rotary part 6 to allow rotation of rotary step-up transformer 15. Rotary step-up transformer 15 takes the so called axial gap configuration where primary part 41 and secondary part 42 axially confront each other over a gap 43.

Figure 7:
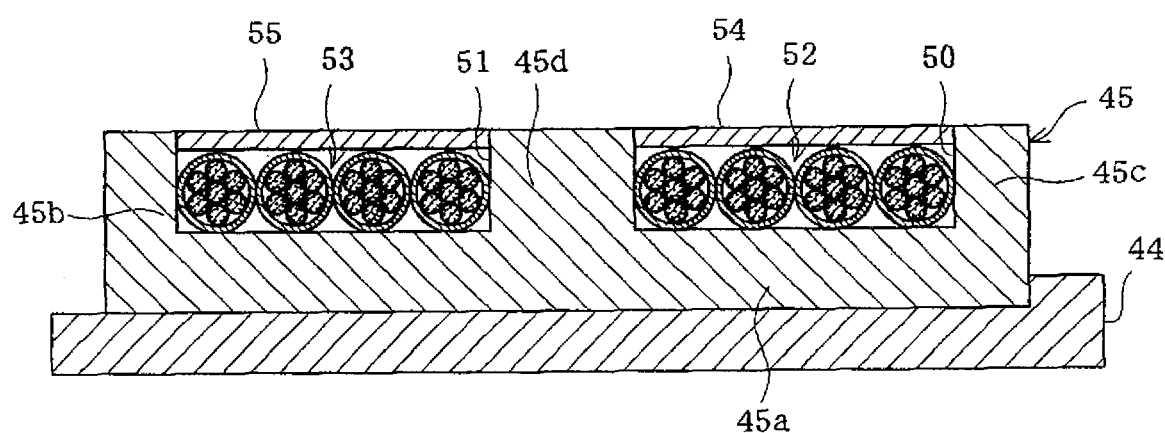
FIG. 7 is a circumferential cross-section of the primary part.

Primary part 41 is configured primarily by a core holder 44, a primary core 45, and primary winding 24 whereas the secondary part 42 is configured primarily by core holder 46, secondary core 47, and secondary winding 27. Core holder 44 of primary part 41 comprises an annular aluminum plate, for example, and is mounted on stationary part 5. On the upper surface of core holder 44, primary core 45 is disposed which is also annular in shape but reduced in width compared to core holder 44. Primary core 45 is made of magnetic material such as magnetic steel sheet or ferrite core. Primary core 45, as shown in FIG. 7, has a couple of linear grooves 50 and 51 which are aligned parallel so as to confront secondary part 42. Groove 50 and 51 define an E-shaped cross section of primary core 45. Primary core 45 has primary winding 24 provided circumferentially along grooves 50 and 51.

Figure 12:
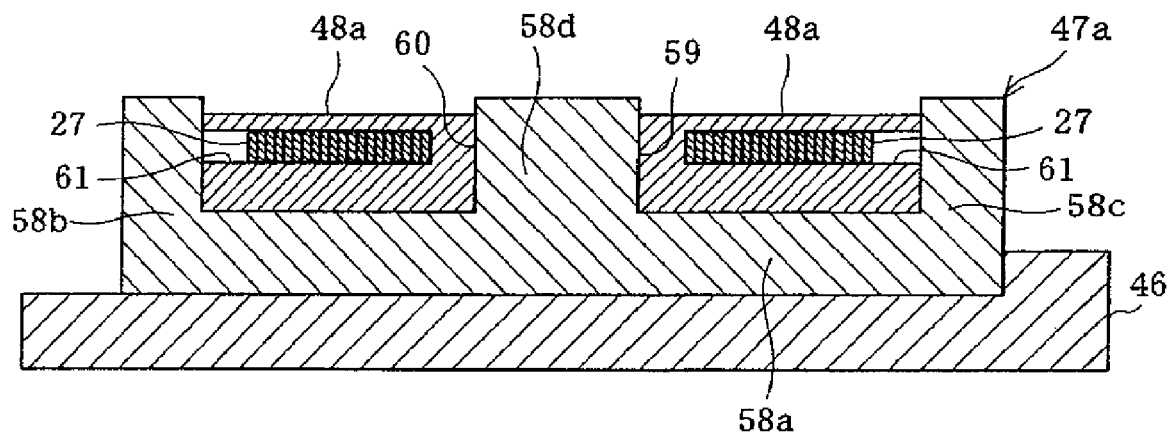
FIG. 12 is a circumferential cross-section of the secondary part.

Core holder 46 at the secondary part 42 is similar in configuration to core holder 44 at primary part 41. Core holder 46 is mounted on rotary part 6 and has a secondary core 47 disposed at the underside of core holder 46. Secondary core 47 comprises a plurality of arc shaped secondary core elements 47a to 47l (corresponding to a plurality of secondary cores). Secondary core elements 47a to 47l are circumferentially isolated by a predetermined spacing. Secondary core elements 47a to 47l, as shown in FIG. 12, have a couple of linear grooves 59 and 60 which are aligned parallel so as to confront primary part 41. Grooves 59 and 60 define the E-shaped cross section of secondary core components 47a to 47l. Each of 12 units of secondary core elements 47a to 47l has secondary winding 27 provided in grooves 59 and 60 via insulation panel. Secondary winding 27 is connected in sequential series between the secondary core elements 47a to 47l. FIG. 3 does not show wiring between the secondary core elements for simplicity.

Gap 43 defined between primary core 45 and secondary core 47 is an air gap having constant width. Rotary transformer 16 being similar in form to rotary step-up transformer 15 is configured in a core-shape. However, rotary transformer 16 having a transformation ratio of 1:1, unlike rotary step-up transformer 15, differs from rotary step-up transformer 15 in winding structure and insulation structure.

Figure 5:
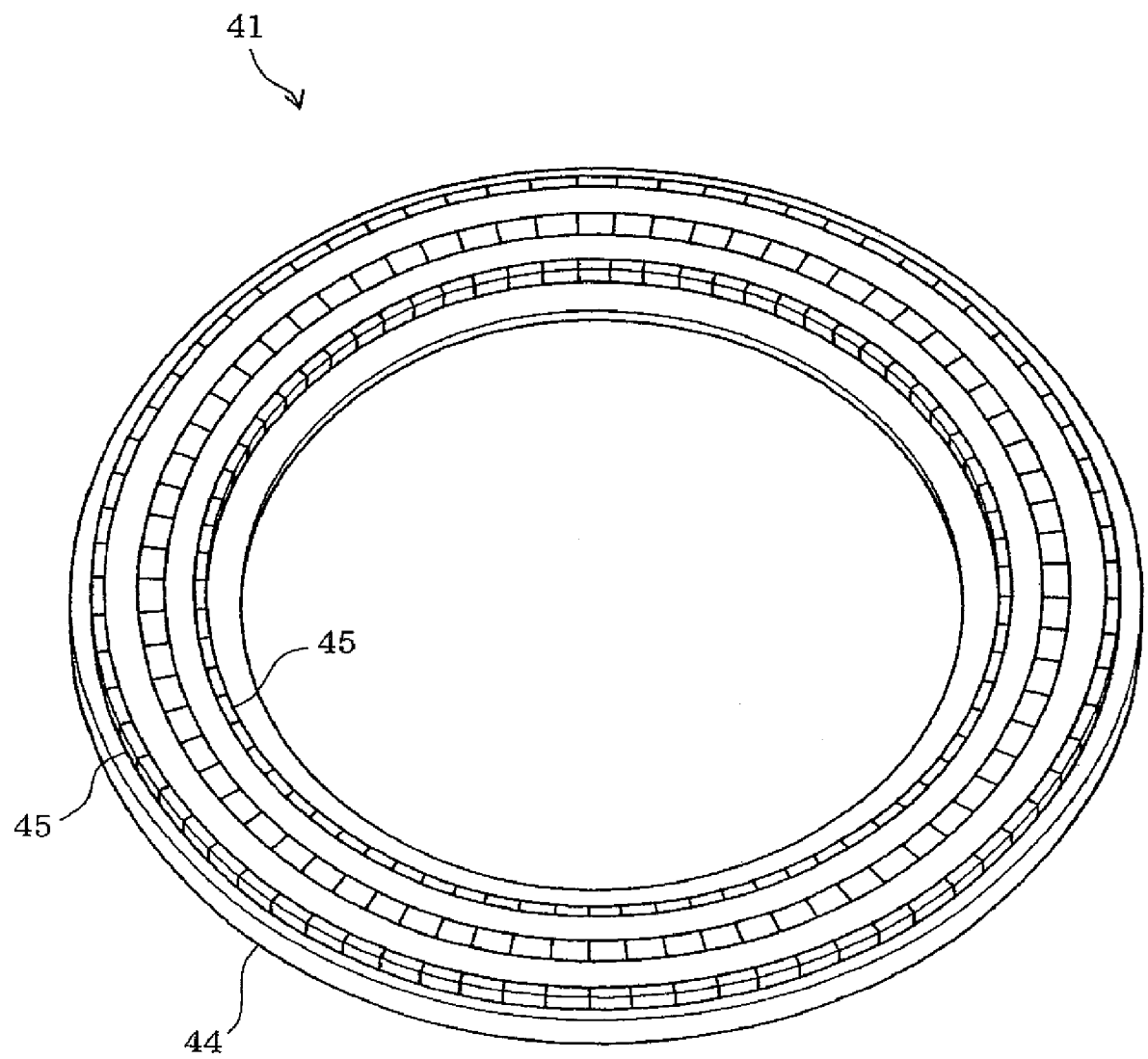
FIG. 5 is a perspective view of a primary part.
Figure 6:
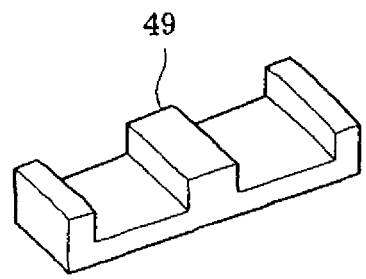
FIG. 6 is an enlarged perspective view of a portion of a primary core.

Next, the configuration of primary part 41 will be described in detail. FIG. 5 is a perspective view of primary part 41. FIG. 7 is a circumferential cross section of primary part 41. Primary core 45, as shown in FIG. 6, is configured by 72 units of primary core elements 49 disposed circumferentially on the upper surface of core holder 44. Each primary core element 49 is configured as an arch having a central angle of 5 degrees, for example, and has an E-shaped cross section as shown in FIG. 6. Primary core element 49 comprises a core element having an E-shaped cross section configured by a bottom wall magnetic path 45a, sidewall magnetic paths 45b and 45c, and a central magnetic path 45d. Sidewall magnetic paths 45b and 45c and central magnetic path 45d correspond to legs.

Primary winding 24 comprises a first wire 52 and second wire 53 each configured by four parallel connected litz wires. First wire 52 is provided along the entire circumference of groove 50 and second wire 53 is provided along the entire circumference of groove 51. First wire 52 and second wire 53, thus, have a turn number of 1. Grooves 50 and 51 are covered by lids 54 and 55 for secure placement of first and second wires 52 and 53 within grooves 50 and 51.

Figure 8:
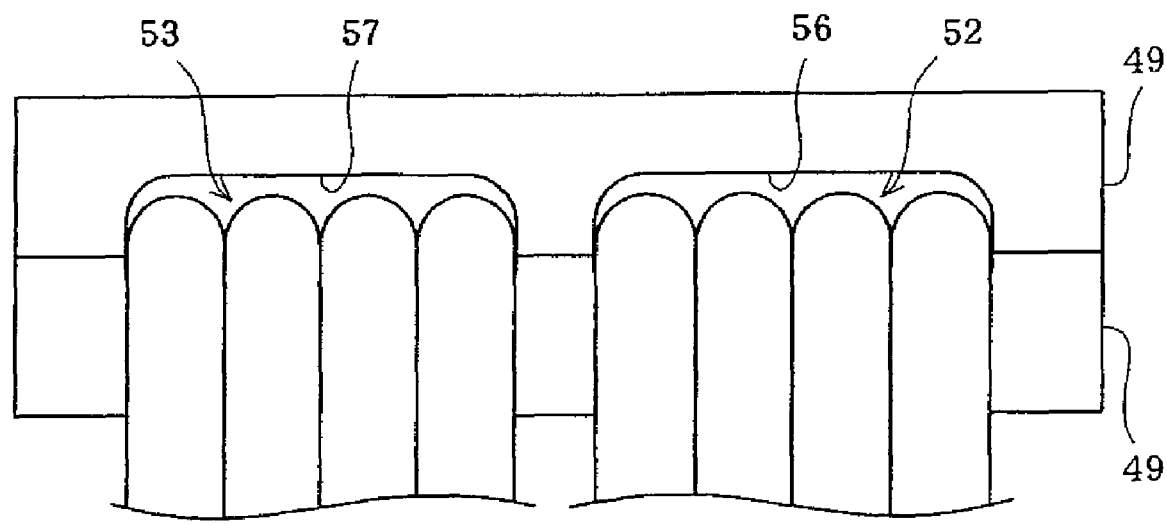
FIG. 8 is a bottom view of the primary part.

FIG. 8 partially depicts the bottom surface of primary part 41. On the bottom surfaces of core holder 44 and primary core 45 elongate outlet holes 56 and 57 are defined to draw first and second wires 52 and 53 wound on primary core 45 to power supply. Outlet holes 56 and 57 are defined on primary core 45 so as to be situated at a portion of joints between primary core elements 49.

Figure 9:
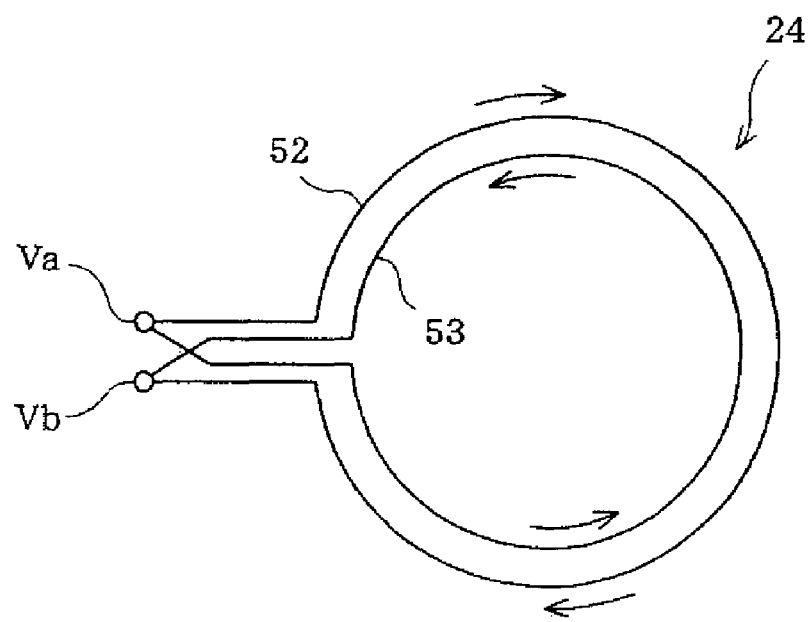
FIG. 9 is a schematic of a primary winding.

FIG. 9 is a schematic of primary winding 24. As can be seen in FIG. 9, first wire 52 and second wire 53 of primary winding 24 are connected in parallel at power supply terminals Va and Vb. First wire 52 extends clockwise from terminal Va to terminal Vb, whereas second wire 53 extends counterclockwise from terminal Va to terminal Vb.

The above described configuration causes a primary current to flow in the direction indicated by the arrow shown in FIG. 9 when high frequency voltage is applied on primary winding 24 from inverter circuit 22 via power supply terminals Va and Vb. The primary current flow is branched into a first current path flowing through first wire 52 and a second current path flowing through second wire 53. The primary current flowing through the first current path and the primary current flowing through the second current path flow in opposite directions. This means that first wire 52 and second wire 53 neighboring each other over central magnetic path 45d of primary core 45 have opposing primary current flows.

Figure 10:
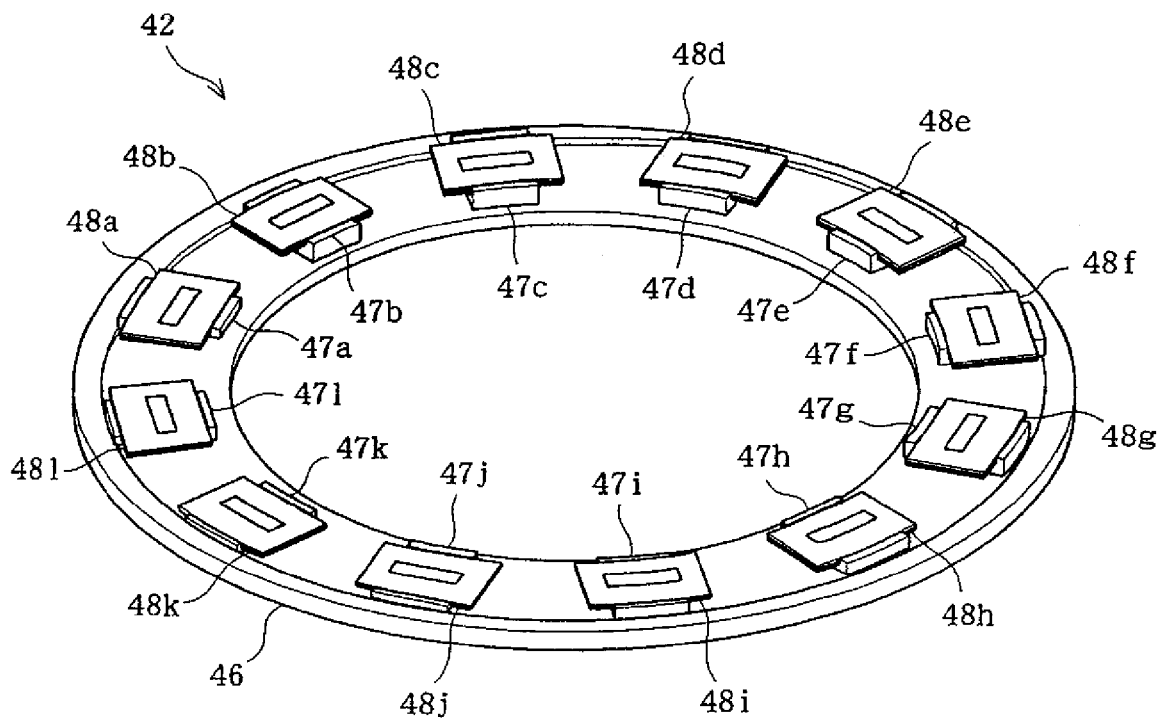
FIG. 10 is a perspective view of the secondary part.
Figure 11:
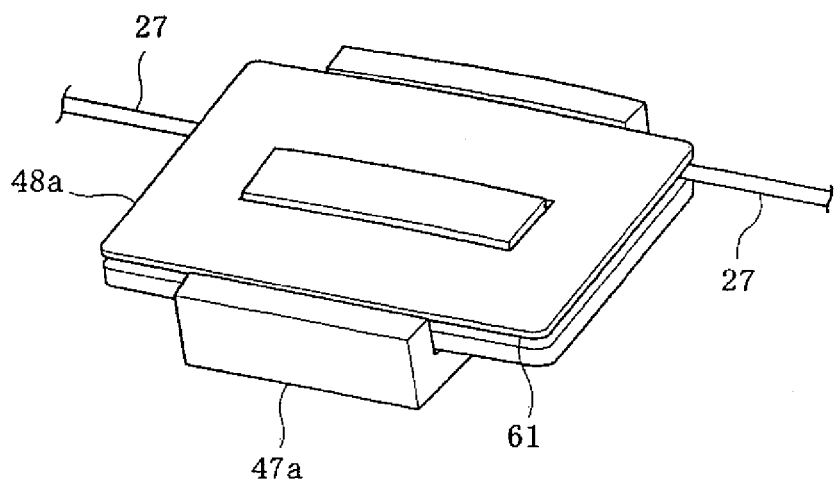
FIG. 11 is an enlarged perspective view of a portion of the secondary part.

Next, the configuration of secondary part 42 will be described in detail. FIG. 10 is a perspective view of secondary part 42 and FIG. 11 is a partially enlarged view of FIG. 10. As can be seen in FIG. 10, secondary part 42 has a secondary core comprising 12 units of secondary core elements 47a to 47l which are circumferentially disposed on the upper surface of core holder 46 at constant 30 degree intervals. Each secondary core elements 47a to 47l is similar in shape to primary core element 49 shown in FIG. 6 exhibiting an arch shape. The difference lies in the central angle of the arc which is 10 degrees, for example, in the case of secondary core elements 47a to 47l. The cross section of secondary core elements 47a to 47l is also E-shaped.

FIG. 12 is a circumferential cross sectional view of a secondary part 42 (secondary core element 47a) Secondary core element 47a disposed on the upper surface of core holder 46 comprises a bottom wall magnetic path 58a, sidewall magnetic paths 58b and 58c, and a central magnetic path 58d.

Secondary core element 47a and secondary winding 27 are insulated by an insulation panel 48a. Insulation panel 48a is rectangular in form and has a rectangular opening at the center. Insulation panel 48a is grooved on all sides so that its side surfaces define a groove 61 for receiving secondary winding 27. Insulation panel 48a receiving secondary winding 27 at groove 61 is assembled to secondary core element 47a by fitting central magnetic path 58d into the central opening. Secondary winding 27 is configured by a rectangular litz wire, for example and is wound on groove 61 of insulation plate 48a as described earlier.

Figure 13:
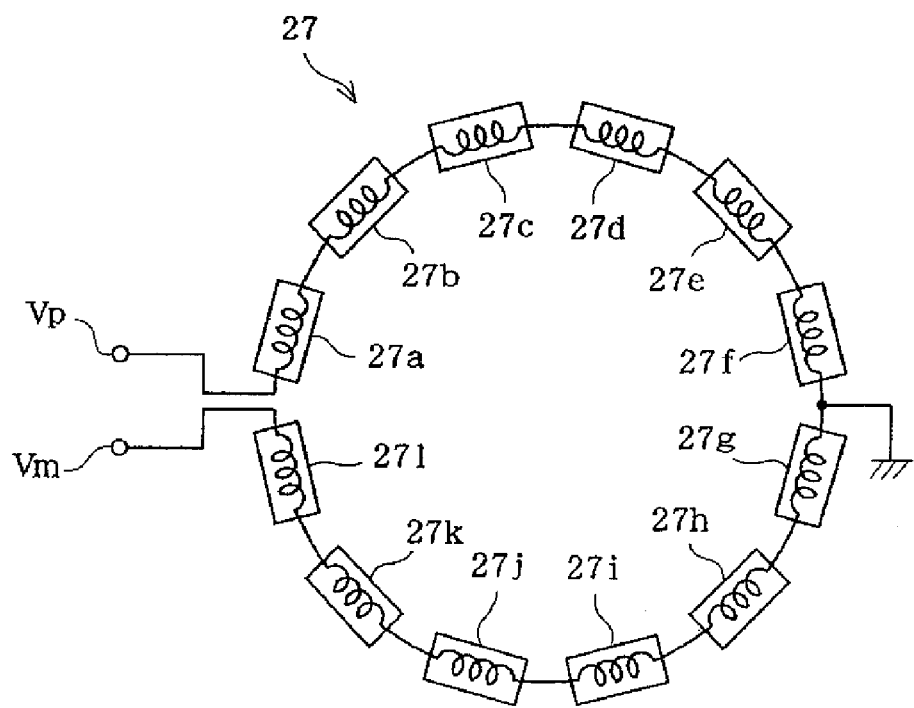
FIG. 13 is a schematic of a secondary winding.

FIG. 13 is a schematic of secondary winding 27. In FIG. 13, secondary core elements 47a to 47l wound with secondary winding 27 are represented as windings 27a to 27l. Secondary winding 27 is earthed at the intermediate portion, in other words, at the interconnect of winding 27f and 27g. Secondary core 47 is also earthed.

For instance, if 9 kV of voltage is generated between the terminals of secondary winding 27 with terminal Vm being earthed, voltage level at terminal Vm indicates 0V and voltage level at terminal Vp indicates +9 kV. Thus, difference in potential between the earthed secondary core 47 and secondary winding 27 (windings 27a to 27l) is maximized to 9 kV at terminal Vp.

Contrastingly, if the intermediate portion is earthed as described in FIG. 13 of the present exemplary embodiment, and voltage level of 9 kV is similarly generated between the terminals of secondary winding 27, terminal Vp indicates a voltage level of +4.5 kV whereas terminal Vm indicates a voltage level of −4.5 kV. In this case, the difference in potential between secondary core 47 and windings 27a to 27f having relatively higher potential amounts to 4.5 kV at maximum at terminal Vp. Likewise, the difference in potential between secondary core 47 and windings 27g to 2ll having relatively lower potential (located relatively closer to terminal Vm) amounts to 4.5 kV at maximum at terminal Vm. This means that potential difference between secondary winding 27 and secondary core 47 can be reduced by earthing the intermediary portion of secondary winding 27.

The above described configuration provides the following operation and effect.

Three phase AC voltage (415V) supplied from AC power source 20 is rectified by rectifier circuit 21 to produce a DC output which in turn is converted into high-frequency voltage by inverter circuit 22. The high-frequency voltage outputted from inverter circuit 22 is applied to primary winding 24 of rotary step-up transformer 15 to generate a high-frequency current flow through first and second wires 52 and 53.

When primary current flows clockwise as viewed in FIG. 3 through first wire 52 and counter clockwise through second wire 53 situated radially inward relative to first wire 52, magnetic flux $\phi 1$ and $\phi 2$ are generated as represented by broken lines in FIG. 4. To describe more specifically with reference to FIG. 4 depicting the confrontation of primary core 45 with secondary core 47, a counterclockwise magnetic flux $\phi 1$ occurs at the right side of the confrontation and clockwise magnetic flux $\phi 2$ occurs at the left side of the confrontation. Magnetic flux $\phi 1$ and $\phi 2$ are passed around the outer periphery and inner periphery of secondary core elements 47a to 47l, respectively. Thus, voltage is induced at windings 27a to 27l respectively wound on secondary core elements 47a to 47l. Since windings 27a to 27l are connected in sequential series, a secondary voltage amounting to the sum of voltage occurring at windings 27a to 27l occurs between the terminals of secondary winding 27.

The above described magnetic coupling transmits power to the secondary side to cause high frequency voltage to occur between the terminals of the secondary winding 27 which is 150 times or greater in magnitude as compared to the high frequency voltage applied on primary winding 24. The high frequency voltage occurring between the terminals of secondary winding 27 is rectified by rectifier circuit 29.

Rectifier circuit 29 outputs DC voltage to be applied on X-ray tube 7. The level of voltage required to radiate X-ray from X-ray tube 7 is approximately 70 kV to 150 kV, though it may vary depending upon the type X-ray tube 7 (See General Requirements for High-voltage Generators of Medical X-ray Apparatus: JIS Z 4702). Thus, step-up ratio of rotary step-up transformer 15 is set to output 70 kV of DC voltage, the lowermost limit of the above described range, from rectifier circuit 29.

AC voltage level of AC power source 20 is 415V. However, considering the voltage drop occurring at rectifier circuit 21, inverter circuit 22, rotary step-up transformer 15 and rectifier circuit 29, rotary step-up transformer 15 requires step-up ratio setting of at least "150". In the present exemplary embodiment, turns ratio of primary winding 24 and secondary winding 27 is set to obtain a step-up ratio of "23". Thus, voltage occurring at each of windings 27a to 27l is 23 times greater than the voltage of primary voltage. The secondary voltage obtained by sequential series connection of voltage occurring at windings 27a to 27l amounts to 276 times (=23×12) of primary voltage. The above described settings of step-up ratio for rotary step-up transformer 15 allows DC voltage ranging from 70 kV to 150 kV to be applied on X-ray tube 7 for radiation of X-ray beams.

DC output from rectifier circuit 21 is supplied to inverter circuit 23 as well. When high frequency voltage outputted from inverter circuit 23 is applied on primary winding 25 of rotary transformer 16 to cause high frequency current flow, magnetic flux is generated as was the case for rotary step-up transformer 15. The magnetic flux transmits power to the secondary side to generate a high frequency voltage between the terminals of secondary winding 28 that equals the voltage level generated at primary winding 25. The high frequency voltage generated between the terminals of secondary winding 28 is rectified by rectifier circuit 30. DC voltage outputted from rectifier circuit 30 is converted into DC voltage of desired voltage level by control power source 14 and thereafter supplied to components such as X-ray detector 8 and cooler 9.

As described above, non-contact transmission of power to rotary part 6 from stationary part 5 eliminates maintenance for component wear-out, which was formerly required in contact transmission, thereby improving system reliability. Non contact transmission also contributes to noise-reduction which reduces stress suffered by the patient when the device is used in medical applications. Further, since a heavy-weight high-voltage transformer no longer needs to be provided at rotary part 6, rotary part 6 can be reduced in size and weight, which in turn reduces the centrifugal force upon rotation of rotary part 6. The reduction of centrifugal force allows increase in maximum rotation speed, which improves the quality of the generated image. Weight reduction of rotary part 6 further contributes to reduction of electricity consumption for rotation of rotary part 6.

Further, two transmitting sections have been provided for power supply from stationary part 5 to rotary part 6. Power is supplied to X-ray tube 7 through rotary step-up transformer 15, whereas power is supplied to other components provided at rotary part 6 such as X-ray detector 8 and cooler 9 through rotary transformer 16. Thus, power is supplied constantly to control systems such as X-ray detector 8, cooler 9, and X-ray controller 11, and power supply may be turned ON/OFF for X-ray tube 7 alone. Such configuration allows further reduction in electricity consumption of X-ray CT device 1. Further, even if an abnormal error occurs in the first transmitting section 32, steady power supplied to X-ray controller 11 through the second transmitting section 33 allows abnormal behavior of X-ray tube 7 to be detected by X-ray controller 11 so that operation may be stopped to provide safe and reliable emergency operation. In case of emergency, since steady power is supplied to cooler 9 through the second transmitting section 33, X-ray tube 7 can be cooled on a constant basis to provide reliable operation of the system.

As can be seen in FIG. 2, space enclosed by broken line is available inside rotary part 6. This space may be utilized to provide an additional set of X-ray tube and X-ray detector to reduce the duration of imaging process as well as improve the quality of the generated image.

Yet, further secondary winding 27 of rotary step-up transformer 15 has been earthed at the intermediate portion (the interconnecting point of winding 27f and 27g) to reduce potential difference between secondary winding 27 and the earthed secondary core 47. Such configuration allows the length of insulation provided on the secondary side bearing high level of voltage to be reduced. This consequently reduces the distance between the windings, which in turn reduces primary current. Furthermore, smaller spacing for the winding allows a compact and low cost system.

A secondary core 47 has been configured by twelve arc-shaped secondary core elements 47a to 47l each having a central angle of 10 degrees. Such configuration will reduce the weight the secondary core 47 to ⅓(=10 degrees×12/360 degrees) of the weight of the secondary core 47 and the secondary winding being configured annularly. Thus, secondary core 47 can be configured with less amount of material (magnetic steel sheet or ferrite core) and hence, reduce manufacturing cost.

Since secondary core 47 is configured by a plurality of secondary core elements 47a to 47l, the central angle of the area where primary core 45 and secondary core 47a to 47l confront each other (hereinafter referred to as confronting angle) is reduced. However, first and second wires 52 and 53 constituting primary winding 24 is configured to flow current in the opposite directions. Thus, magnetic flux $\phi 1$ and $\phi 2$ occurring around first and second wires 52 and 53 are passed around the outer periphery and inner periphery of secondary core elements 47a to 47l which provides improved magnetic coupling of the primary side and the secondary side. Thus, output of approximately 120 kW can be obtained which is substantially equivalent to the output produced by an annular secondary core 47 and secondary winding 27.

Secondary core elements 47a to 47l constituting secondary core 47 are uniform in structure. Thus, adjustment can be made on the secondary voltage and output by altering the number of secondary core elements. Such configuration allows manufacturing of X-ray CT device of various output performances without additional investment on preparing casts for manufacturing different types of core elements.

Since secondary core elements 47a to 47l of secondary part 42 is circumferentially disposed at predetermined constant angular interval of 30 degrees, the weight of rotary part 6 can be better balanced with less likelihood of rotational variance occurring at rotary part 6.

First and second wires 52 and 53 are wound all round the perimeter of grooves 50 and 51. Thus, primary current flows almost uninterruptedly, allowing constant magnetic flux $\phi 1$ and $\phi 2$ to occur at primary core 45. Further, level of secondary voltage occurring between the terminals of secondary winding 27 will no longer vary depending on rotational status, consequently stabilizing power supply to the secondary side. In the present exemplary embodiment, primary winding 24 comprising four litz wires is configured in annular form. Thus, primary part 41 can be assembled with greater ease compared to a later described second exemplary embodiment which requires primary winding 24 to be turned back.

A description will be given on a second exemplary embodiment with reference to FIGS. 14 and 15.

The second exemplary embodiment differs from the first exemplary embodiment in that primary part of rotary step-up transformer is modified in structure. FIGS. 14 and 15 correspond to FIGS. 3 and 9 of the first exemplary embodiment and elements that are identical to the first exemplary embodiment are identified with identical reference symbols without further descriptions.

Figure 14:
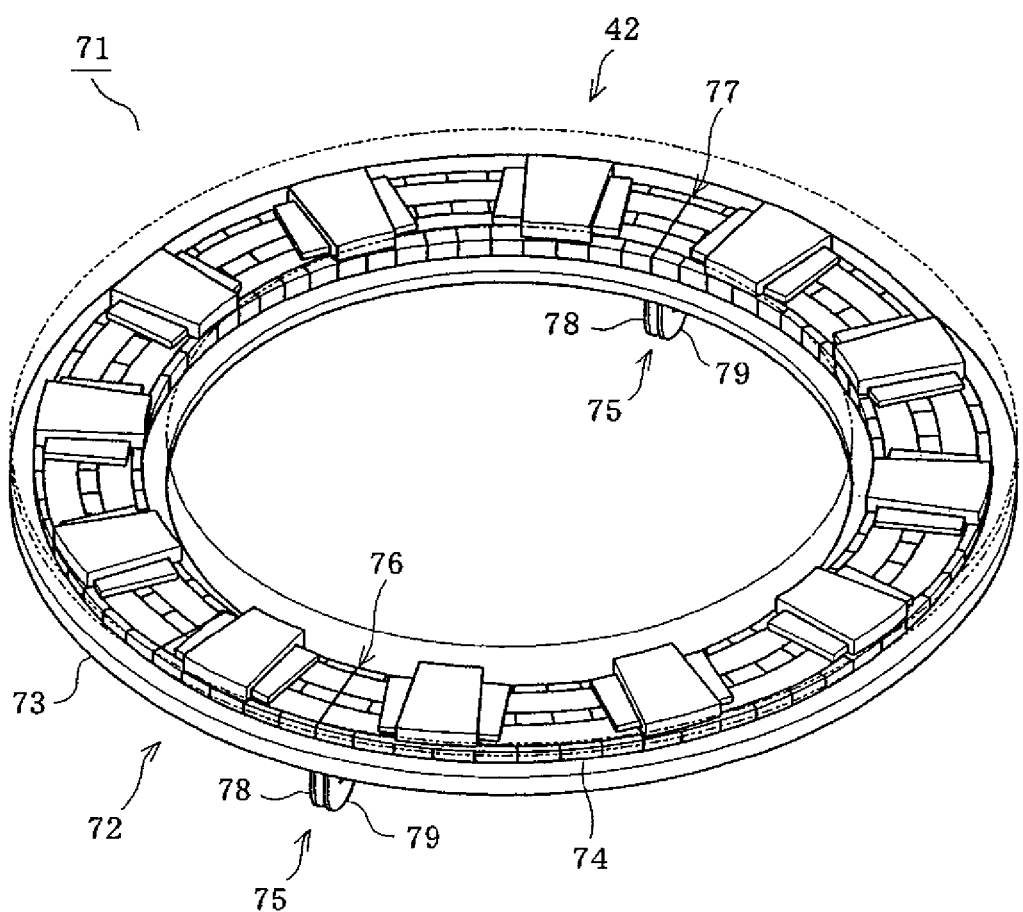
FIG. 14 depicts a second exemplary embodiment of the present disclosure and corresponds to FIG. 3.

FIG. 14 describes a rotary step-up transformer 71 comprising a generally annular and concentric primary part 72 and a secondary part 42. Primary part 72 is configured primarily by a core holder 73, a primary core 74, and a primary winding 75. Core holder 73 and primary core 74 are similar in configuration to core holder 44 and primary core 45 depicted in FIG. 3. Core holder 73 and primary core 74, however differs from core holder 44 and primary core 45 in that slots 76 and 77 for drawing in/out primary winding 75 is provided on the bottom surface.

Primary winding 75 comprises a first wire 78 and a second wire 79 each configured by four parallel connected litz wires. First wire 78 is disposed in engagement with the outer groove (represented by the reference symbol 50 in FIG. 7) of primary core 74 along the semiperimeter from slot 76 providing access to the power supply element to slot 77 situated on the opposite side of slot 76. The first wire 78 is thereafter folded back so as to be disposed in engagement with the inner groove (represented by the reference symbol 51 in FIG. 7) of the primary core 74 along the same semiperimeter. The first wire 78, when making the fold back, is bent downward as viewed in FIG. 14 to protrude from slot 77.

Second wire 79 is disposed in engagement with the inner groove of primary core 74 along the semiperimeter from slot 76 to slot 77. The second wire 79 is thereafter folded back so as to be disposed in engagement with the outer groove of the primary core 74 along the same semiperimeter. The second wire 79, when making the fold back is also bent downward as was the case for the first wire 78.

Figure 15:
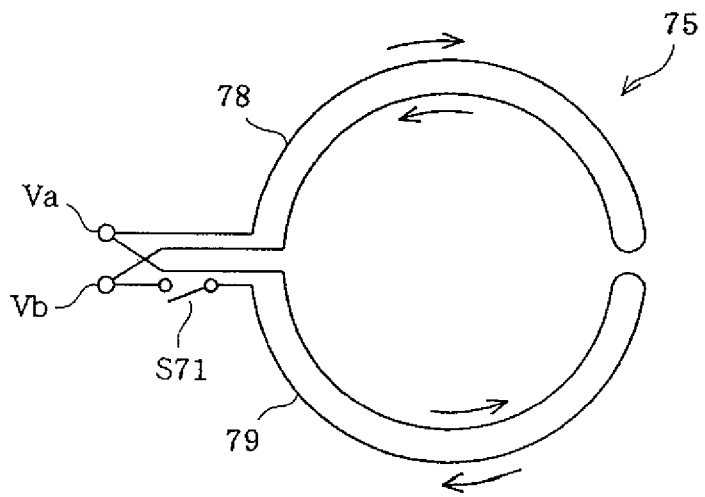
FIG. 15 corresponds to FIG. 9.

FIG. 15 is a schematic of primary winding 75. As can be seen in FIG. 15, first wire 78 and second wire 79 are connected in parallel via power supply terminals Va and Vb. First wire 78 extends clockwise from terminal Va and is folded back counterclockwise to be connected to terminal Vb; whereas second wire 79 extends counterclockwise from terminal Va and is folded back clockwise to be connected to terminal Vb via a switch S71 (not shown in FIG. 14). Switch S71 is provided at a power supply section not shown. Switch S71 is generally turned ON, and by turning OFF switch S71, power can be selectively transmitted to first wire 78 only.

According to the above configuration, when high frequency voltage is applied on primary winding 75 from inverter 22 via power supply terminals Va and Vb, primary current flows as indicated by the arrow in FIG. 15. This means that the present exemplary embodiment also provides a first current path and a second current path, which allow primary current to flow in opposite directions as was the case in the first exemplary embodiment.

The second exemplary embodiment, thus provides the same operation and effect provided in the first exemplary embodiment. X-ray CT device 1 may be used to generate two-dimensional images without rotating the rotary part 6, or may be placed in standby when imaging is not executed. Two dimensional imaging and standby requires less output as compared to output required in normal use when imaging is executed by rotation of rotary part 6. Thus, by switching off switch S71, power can be selectively supplied to first wire 78 only to cut down on electricity consumption.

Figure 16:
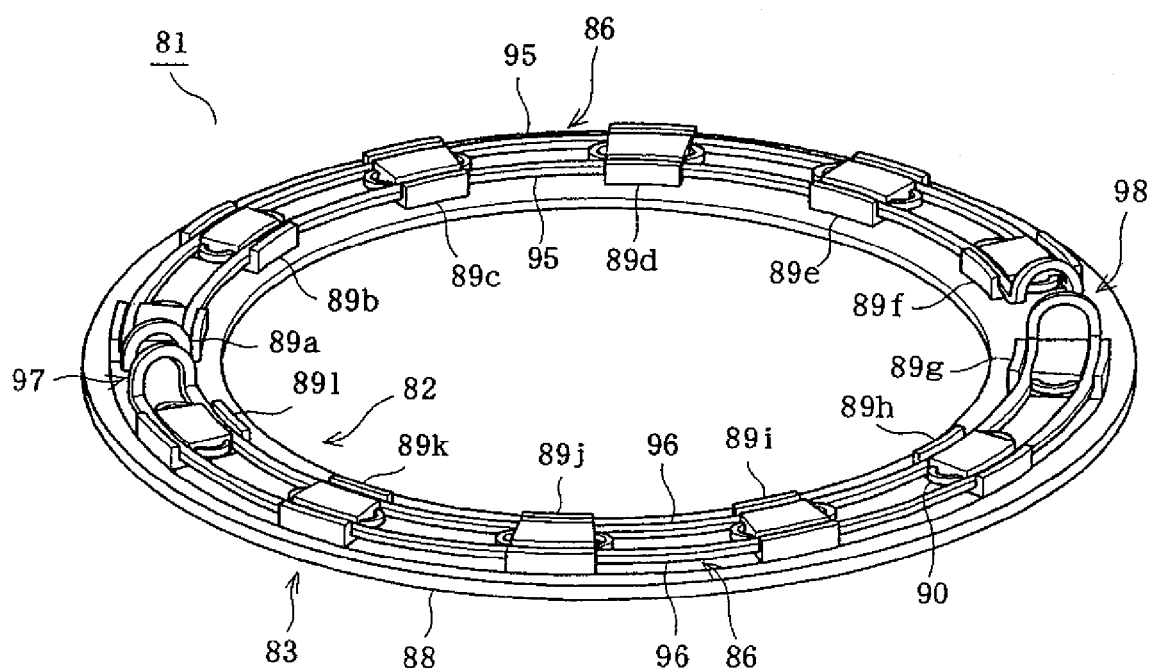
FIG. 16 depicts a third exemplary embodiment of the present disclosure and corresponds to FIG. 3.
Figure 17:
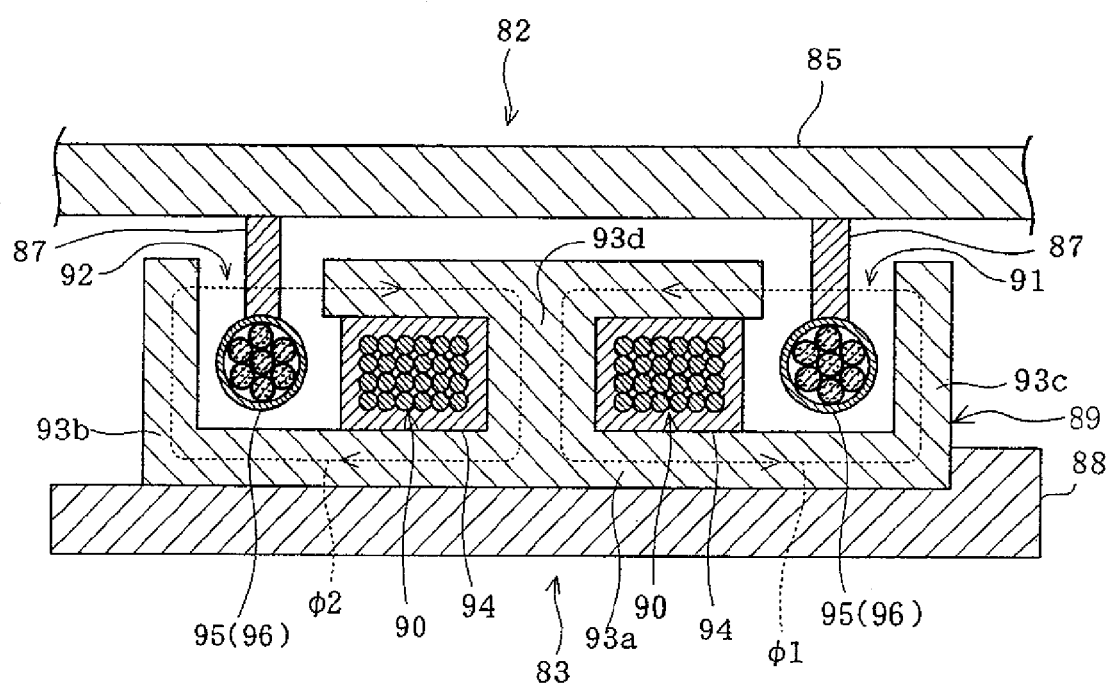
FIG. 17 is a circumferential cross sectional view of the rotary step-up transformer.

Next, a description will be given on a third exemplary embodiment of the present disclosure with reference to FIGS. 16 and 17. FIGS. 16 and 17 correspond to FIGS. 3 and 4 of the first exemplary embodiment and elements that are identical to the first exemplary embodiment are identified with identical reference symbols and will not be described.

Rotary step-up transformer 81 comprises a generally annular and concentric primary part 82 and a secondary part 83. Primary part 82 and secondary part 83 are configured to axially confront each other. Primary part 82 is configured primarily by a fixture frame 85 (not shown in FIG. 16), a primary winding 86 and support 87. Secondary part 83 is configured primarily by a a core holder 88, a secondary core 89, and a secondary winding 90.

Core holder 88 provided at secondary part 83 is annular in form and composed of an aluminum plate. Core holder 88 being mounted on rotary part 6 has secondary core 89 disposed on its upper surface. Secondary core 89 is configured by a plurality of arch shaped secondary core elements 89a to 89l (corresponding to a plurality of secondary cores), each having a central angle of 10 degrees. Secondary core elements 89a to 89l are circumferentially isolated by a constant angle of 30 degrees.

Secondary core 89 is configured by a bottom wall magnetic path 93a, sidewall magnetic paths 93b and 93c, and central magnetic path 93d having a T-shaped cross section that define a couple of open top grooves 91 and 92. Secondary winding 90 is wound on each of the 12 units of secondary core elements 89a to 89l at grooves 91 and 92 (portion surrounded by bottom wall magnetic path 93a and central magnetic path 93d) via an insulation element 94. Secondary windings 90 wound on each of secondary core elements 89a to 89l are interconnected in sequential series. FIG. 16 does not show the wiring between each secondary core elements for simplicity.

Fixture frame 85 provided at primary part 82 is mounted on stationary part 5. Primary winding 86 is supported by fixture frame 85 via support 87 provided on the underside of fixture frame 85. Primary winding 86 comprises a first wire 95 and a second wire 96 which are configured by a litz wire. First wire 95 is disposed along the semiperimeter from slot 97 providing access to the power supply element to slot 98 situated on the opposite side of slot 97. The first wire 95 is thereafter folded back so as to be disposed along the same semiperimeter. The first wire 95, when making the fold back is bent upward.

Second wire 96 is disposed along the semiperimeter from slot 97 to slot 98. The second wire 96 is thereafter folded back so as to be disposed along the same semiperimeter. The second wire 96, when making the fold back is bent upward as was the case for the first wire 95. Primary part 82 and secondary part 83 are assembled so that first and second wires 95 and 96 provided at primary part 82 reside within grooves 91 and 92 of secondary core 89.

Schematic of Primary winding 86 is similar to the schematic of primary winding 75 of the second exemplary embodiment shown in FIG. 15. That is, first and second wires 95 and 96 are connected parallel via the power supply terminals. Thus, the present exemplary embodiment also form the first and the second current paths that allow primary current to flow in opposite directions as was the case in the first exemplary embodiment.

When primary current flows clockwise as viewed in FIG. 16 through first wire 95 and counterclockwise through second wire 96 situated radially inward relative to first wire 95, magnetic flux $\phi 1$ and $\phi 2$ are generated as represented by broken lines in FIG. 17. To describe more specifically with reference to FIG. 17 depicting the confrontation of primary part 82 with secondary part 83, a counterclockwise magnetic flux $\phi 1$ occurs at the right side of the confrontation and clockwise magnetic flux $\phi 2$ occurs at the left side of the confrontation. Thus, voltage is induced at windings respectively wound on secondary core elements 89a to 89l as was the case in the first exemplary embodiment. Since windings are connected in sequential series, a secondary voltage amounting to the sum of voltage occurring at windings occurs between the terminals of secondary winding 90. Thus, the third exemplary embodiment obtains the same operation and effect provided in the first and the second exemplary embodiments.

A description will be given hereinafter on a fourth exemplary embodiment with reference to FIGS. 18 to 20.

The fourth exemplary embodiment differs from the first exemplary embodiment in the configuration of the secondary part of the rotary step-up transformer. Elements that are identical to the first exemplary embodiment are represented by identical reference symbols without detailed descriptions. The secondary part of the fourth exemplary embodiment differs form secondary part 42 of the first exemplary embodiment in the configuration of the insulation panel for providing insulation between the secondary core and the secondary winding and the configuration of the secondary winding. An exemplary description will be given hereinafter on an insulation panel being assembled with secondary core elements 47a shown in FIG. 11.

Figure 18:
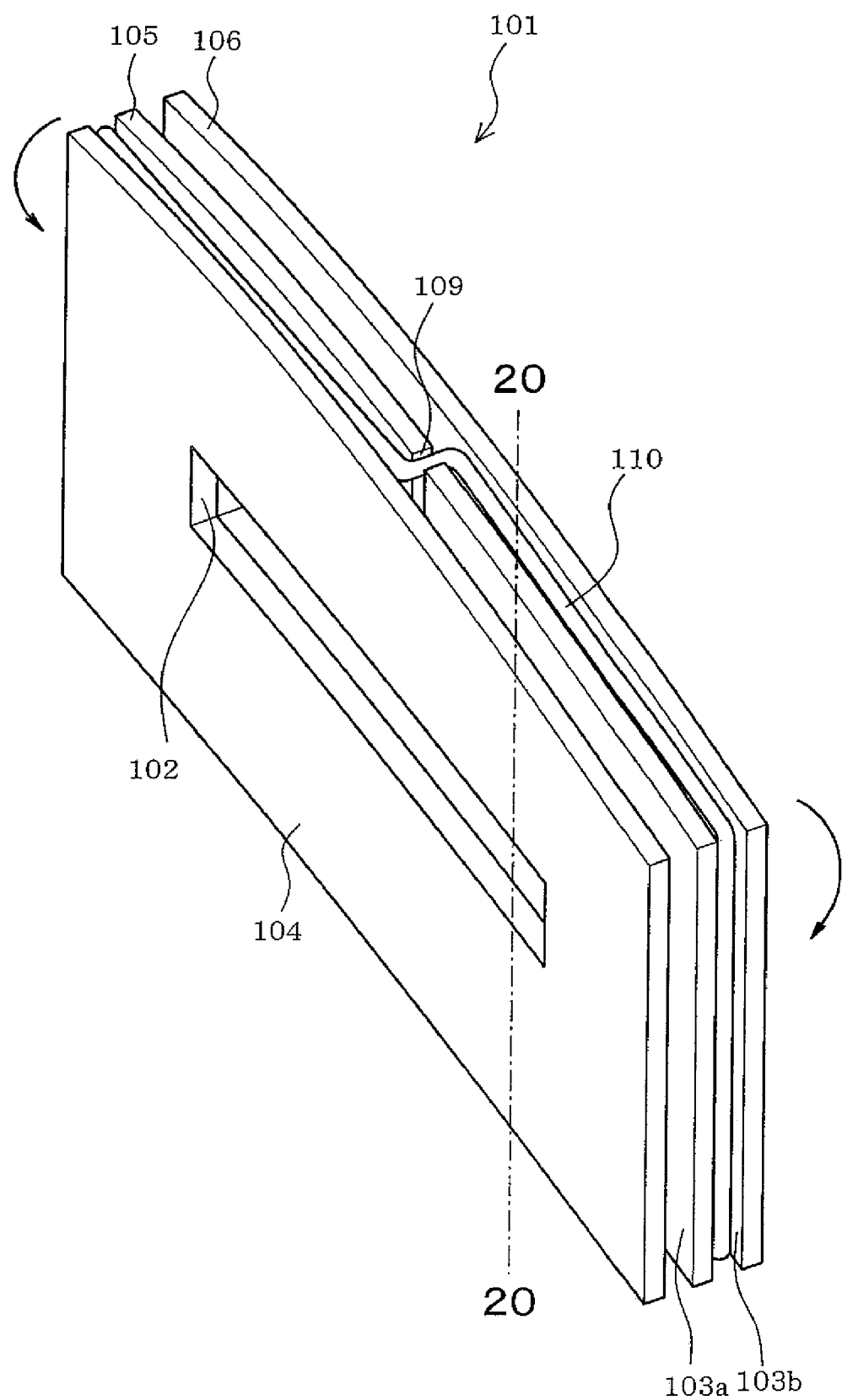
FIG. 18 depicts a fourth exemplary embodiment of the present disclosure providing a perspective view of an insulation panel.
Figure 19:
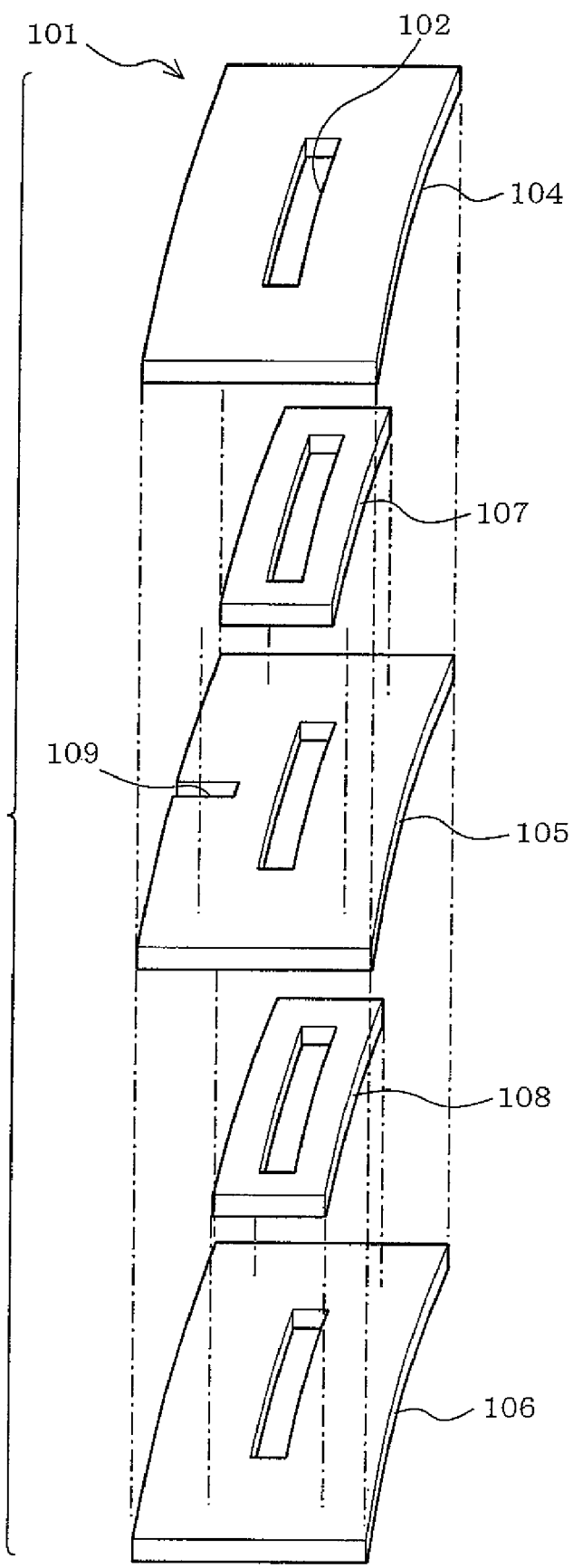
FIG. 19 is an exploded view of the insulation panel.

FIG. 18 is a perspective view depicting the configuration of an insulation panel 101 and FIG. 19 is an exploded view of insulation panel 101. FIG. 20 is a cross sectional view taken along line 20-20 of FIG. 18. Insulation panel 101 has a central opening 102 defined at its center for allowing fitting of central magnetic path 58d (corresponding to a central leg) of secondary core element 47a. Insulation panel 101 has a side groove 103 defined on all sides that extends from the edge of the perimeter to the proximity of the opening 102. Insulation panel 101 is assembled with secondary core element 47a by receiving central magnetic path 58d at its opening 102 while being partially engaged within grooves 59 and 60 of secondary core elements 47a.

Insulation panel 101 is provided with a top panel 104, a middle panel 105, a bottom panel 106, and spacer panels 107 and 108 each being rectangular in form and provided with an opening at its center. Top panel 104, middle panel 105, and bottom panel 106 are identical in shape except that middle panel 105 has a recess defined on it that runs from the central edge of one of its long sides that communicates with the bottom of side groove 103. Spacer panels 107 and 108 are identical in form. The location of recess 109 is not limited to the location shown in FIGS. 18 and 19, but may be formed in any position if it provides communication from the edge of middle panel 105 to the bottom of side groove 103.

Insulation panel 101 is configured by stacking top panel 104, spacer panel 107, middle panel 105, spacer panel 108 and bottom panel 106 in listed sequence, thus defining side groove 103 between top panel 104 and bottom panel 106. The end surfaces of spacer panels 107 and 108 define the bottom of side groove 103. Side groove 103 is partitioned into upper space and lower space by middle panel 105 situated between top panel 104 and bottom panel 106. Stated differently, side groove 103 is divided into a first side groove 103a defined between top panel 104 and middle panel 105 and a second side groove 103b defined between middle plate 105 and lower plate 106.

Secondary winding 110 comprises a round litz wire. Secondary winding 110 is wound between top panel 104 and middle panel 105 and is also wound between middle panel 105 and bottom panel 106 through recess 109. Top panel 104, middle panel 105, bottom panel 106, and spacer panels 107 and 108 are configured by a plurality of heat resistive insulation sheets pressed together. Insulation panel 101 may alternatively comprise a resin mold.

Next, a description will be given on a method in which secondary winding 110 of the present exemplary embodiment is wound. First, a portion of the wiring is introduced into recess 109. Then, originating from the portion of the wiring introduced in recess 109 (corresponding to start point), the segment of the wiring extending in one direction is wound on first side groove 103a so as to expand radially outward from the bottom of the side groove 103a toward the outer periphery of insulation panel 101. The above described direction of winding represents the counterclockwise direction as viewed in FIG. 18. Similarly, originating from the portion of the wiring introduced in recess 109, the segment of the wiring extending in the other direction is wound on second side groove 103b so as to expand radially outward from the bottom of the side groove 103a toward the outer periphery of insulation panel 101. This time, the above described direction of winding represents the clockwise direction as viewed in FIG. 18. Either of winding of secondary winding 110 on first side groove 103a or on second side groove 103a may precede the other. Alternatively, the two winding steps may be executed simultaneously.

According to the above described method of winding, secondary winding 110 is wound in opposite directions when being wound on first side groove 103a and second side groove 103b, respectively. Thus, the secondary current flows in the same direction when flowing through the portion of secondary winding 110 wound on first side groove 103a and second side groove 103b.

The fourth exemplary embodiment, thus also provides the same operation and effect provided in the first exemplary embodiment. Difference in potential of secondary winding 110 wound on each insulation panel 101 maximizes when compared at the start of winding and the end of winding. Thus, if voltage at either the start or end of winding indicates a low level voltage, the other extreme indicates a high level voltage. The fourth exemplary embodiment provides a middle panel 105 to reside between the start of winding and the end of winding. Thus, the capacity of insulation between the low level voltage portion and the high level portion of the secondary winding 110 wound on each insulation panel 101 can be improved. For instance, under the configuration described in the first exemplary embodiment, partial discharge inception voltage at the secondary winding is approximately 800V, whereas in the fourth exemplary embodiment, partial discharge inception voltage is 5 kV. Adjustment may be made on the insulation capacity by altering the thickness and material of middle panel 105. Further, the location at which secondary winding 110 is drawn out at winding start and winding end can be configured as required. This flexibility provides greater ease in the wiring of secondary winding 110 between each insulation panel 101.

A description will now be given on a fifth exemplary embodiment with reference to FIGS. 21 to 24.

The fifth exemplary embodiment differs from the forth exemplary embodiment in the configuration of the insulation panel provided at the secondary part for effecting insulation between secondary core and secondary winding. Elements that are identical to the foregoing exemplary embodiments will be described with identical reference symbols without detailed descriptions.

Figure 20:
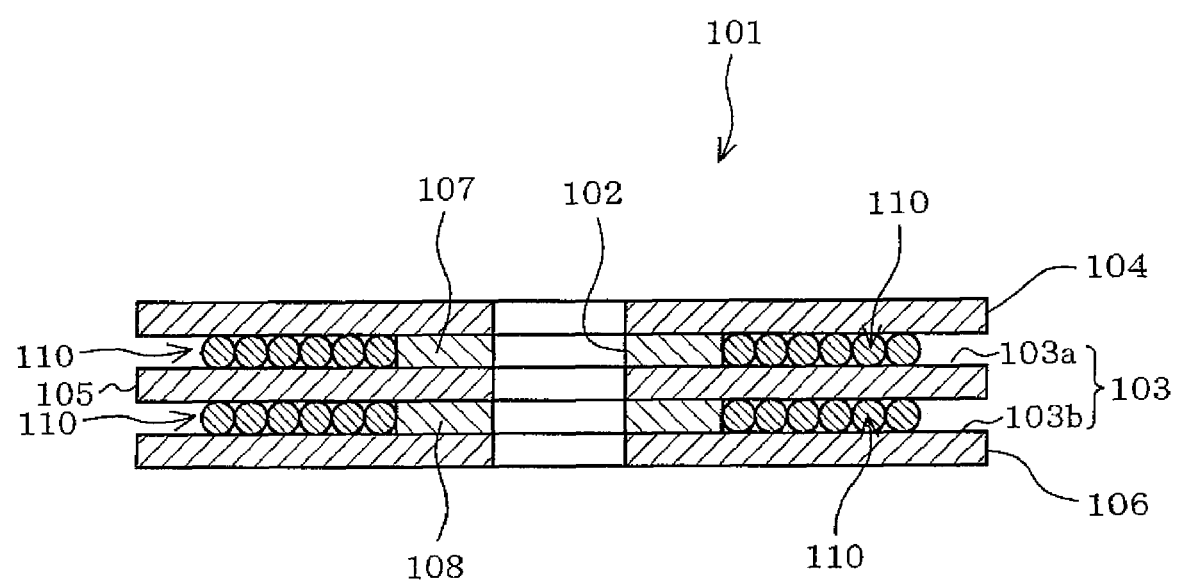
FIG. 20 is a cross sectional view taken along line 20-20 of FIG. 18.
Figure 21:
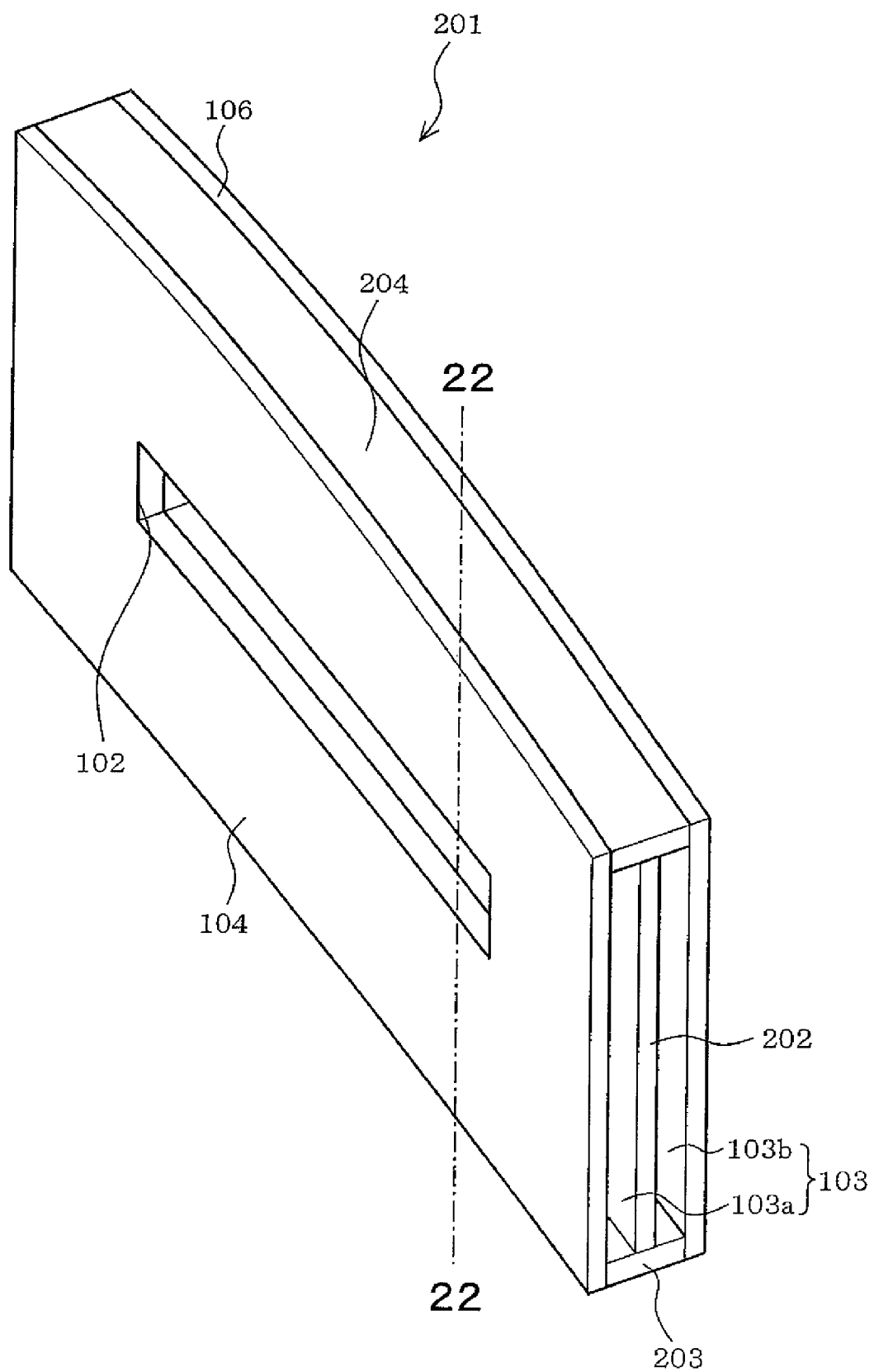
FIG. 21 depicts a fifth exemplary embodiment of the present disclosure and corresponds to FIG. 18.
Figure 22:
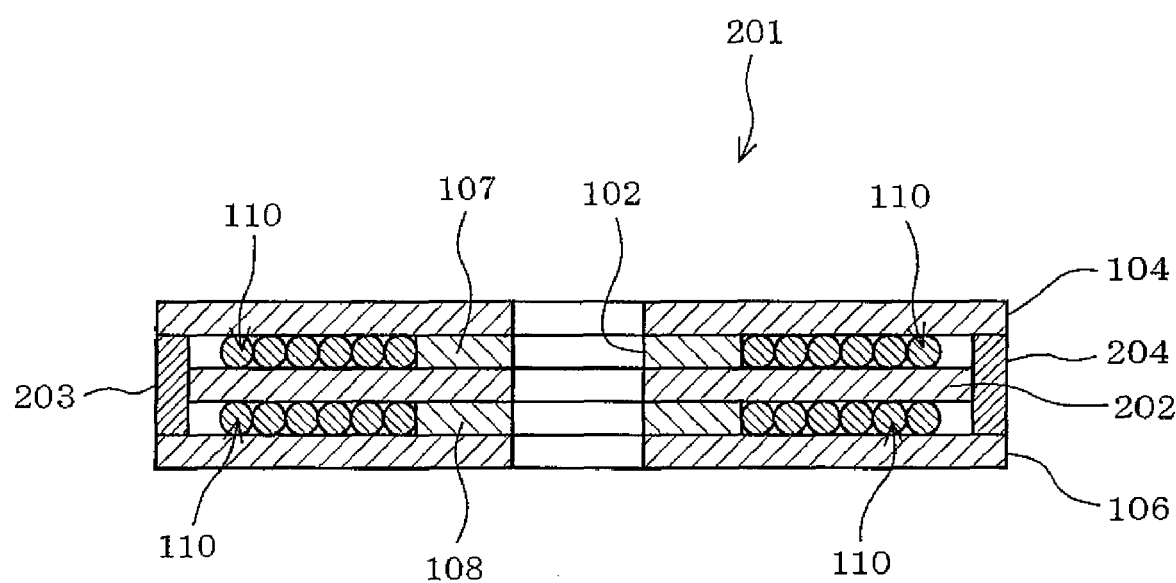
FIG. 22 corresponds to FIG. 20.

FIGS. 21 and 22 correspond to FIGS. 18 and 20 of the fourth exemplary embodiment and depict the configuration of an insulation panel 201. Insulation panel 201 comprises a top panel 104, a middle panel 202, a bottom panel 106, and spacer panels 107 and 108. Middle panel 202 has shorter lateral length as viesed in FIG. 22 as compared to middle panel 105 of the fourth exemplary embodiment.

Insulation panel 201 is provided with insulating elements 203 and 204 for enclosing the inner and outer peripheral side grooves 103 of insulating panel 201. Stated differently, insulation element 203 is provided between sidewall magnetic path 58b (corresponding to an inner leg) of secondary core element 47a and secondary winding 110, whereas insulation element 204 is provided between sidewall magnetic path 58c (corresponding to an outer leg) of secondary core element 47a and secondary winding 110. Insulating elements 203 and 204 are assembled with insulating panel 201 after installing secondary winding 110 inside groove 103 of insulation panel 201.

Figure 23:
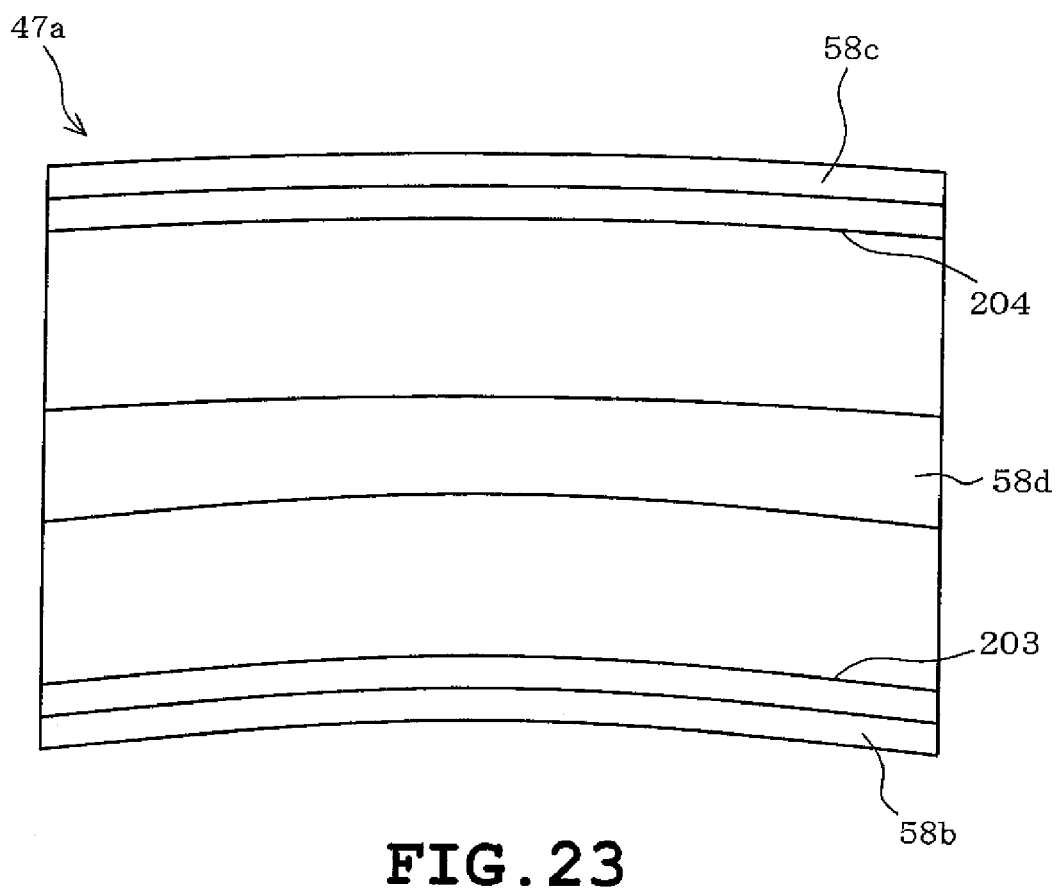
FIG. 23 is a top view of a secondary core element according to a modified view of the present disclosure.
Figure 24:
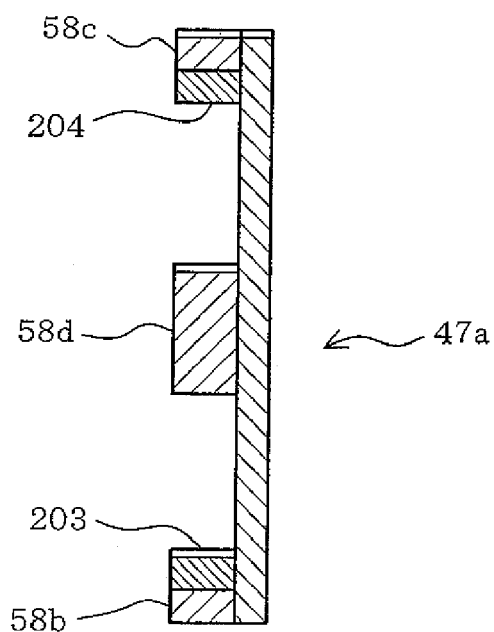
FIG. 24 is side view of the secondary core element.

FIGS. 23 and 24 depict modifications to the fifth exemplary embodiment providing a top view and a side view of secondary core element 47a. As can be seen in FIGS. 23 and 24, insulation elements 203 and 204 may alternatively be provided on the side surfaces of sidewall magnetic paths 58b and 58c of secondary core element 47a. In such case, insulation elements 203 and 204 may be molded integrally with secondary core element 47a. Such configuration facilitates assembly of the secondary part and also improves insulation capacity as will be described afterwards.

The modified exemplary embodiments also provide the same operation and effect provided by the fourth exemplary embodiment. Moreover, provision of insulation elements 203 and 204 between sidewall magnetic paths 58b and 58c of secondary core element 47a and secondary winding 110 offers improved insulation capacity. For instance, required insulation capacity can be obtained even if secondary winding is loosely wound such that secondary winding 110 and secondary core elements 47a are disposed relatively closer. Insulation elements 203 and 204 of the modified exemplary embodiments may be applied to secondary part 42 of the first exemplary embodiment.

The present disclosure is not limited to the above described and shown exemplary embodiments but may be modified or expanded as follows.

Power supply from stationary part 5 to rotary part 6 need not be carried out through two transmitting sections. Rotary transformer 16, inverter 23, and rectifier 30, for example, need not be provided. Under such configuration, power supplied from stationary part 5 via rotary step-up transformer 15 can be supplied to elements provided at rotary part 6 such as a cooler after reducing the level of voltage by a power supply circuit.

If sufficient spacing can be obtained for insulation at the primary side of rotary step-up transformer 15, the intermediate portion of the secondary winding need not be earthed.

The number of secondary core elements is not limited to 12 but is variable depending on the requirements of X-ray CT device 1. When altering the number of secondary core elements, the interval spacing may be altered accordingly. Secondary core elements 47a to 47l may be disposed within an arc-shaped area taking a specific central angle. For instance, 12 units of secondary core elements 47a to 47l may be disposed within an arc-shaped area having a central angle of 180 degrees. According to such configuration, secondary core elements generating high level of voltage, can be interconnected with less wiring, consequently cutting down on wire loss and simplifying the insulation structure at the secondary part 42.

Secondary core elements described as being arc-shaped in the foregoing exemplary embodiments may be rectangular in form, for example, if they can be disposed circumferentially. Primary core element 49 and secondary core elements 47a to 47l may be configured by assembling a couple of rectangular core element (having magnetic path of constant width) each having a single groove defined on it.

In one exemplary embodiment, rotary step-up transformer 71 includes a primary winding 75 configured by first and second wires 78 and 79 which are each disposed circumferentially about the semi perimeters (180 degrees). Alternatively, the primary winding may be configured by 4 windings each disposed circumferentially about the quarter perimeter (90 degrees). By providing a switch capable of controlling power transmission to the 4 windings power consumption may be reduced by approximately 75% at maximum.

The foregoing description and drawings are merely illustrative of the principles of the present disclosure and are not to be construed in a limited sense. Various changes and modifications will become apparent to those of ordinary skill in the art. All such changes and modifications are seen to fall within the scope of the disclosure as defined by the appended claims.

What is claimed is:

1. An X-ray CT device, comprising:
a stationary part;
a rotary part provided rotatably relative to the stationary part;
an X-ray tube being provided at the rotary part and that radiates X-ray beams on an object of imaging;
an X-ray detector being provided at the rotary part so as to oppose the X-ray tube, and that detects the X-ray beams passed through the object;
an image processor that generates cross-sectional images of predetermined portions of the object based on a detection signal outputted from the X-ray detector;
a display that shows the cross-sectional images based on output signals delivered from the image processor;
a rotary step-up transformer that steps up AC voltage by an AC power supply, the rotary step-up transformer including a primary part and a secondary part, the primary part being annular in form and being provided at the stationary part and including a primary winding being provided circumferentially, and the secondary part being provided at the rotary part so as to confront the primary part over a gap and including a plurality of secondary cores disposed circumferentially and a secondary winding configured by a plurality of windings each being wound on each of the secondary cores, the windings being interconnected in series; and
a rectifier circuit that generates DC voltage by rectifying AC voltage occurring between terminals of the secondary winding.

2. The X-ray CT device according to claim 1, wherein the primary winding is configured to define a first current path allowing primary current to flow circumferentially and a second current path being parallel to the first current path and allowing primary current to flow opposite the first current path.

3. The X-ray CT device according to claim 2, wherein the primary winding comprises a first wire annularly disposed to define the first current path and a second wire annularly disposed to define the second current path that are connected parallel.

4. The X-ray CT device according to claim 3, wherein the primary part includes an annular primary core having three legs that define a couple of circumferentially extending grooves therebetween to define an E-shaped cross section, and wherein the first wire is disposed in engagement with one of the grooves along an entire perimeter, and wherein the second wire is disposed in engagement with a remaining other of the grooves along the entire perimeter.

5. The X-ray CT device according to claim 2, wherein the primary winding comprises a first wire and a second wire connected parallel, the first wire being disposed along a first semiperimeter to define the first current path and being folded back to be disposed along the first semiperimeter to define the second current path, the second wire being disposed along a second semiperimeter to define the second current path and being folded back to be disposed along the second semiperimeter to define the first current path.

6. The X-ray CT device according to claim 5, wherein the primary part includes an annular primary core having three legs that define a circumferentially extending first groove and second groove therebetween to define an E-shaped cross section, and wherein the first wire is disposed in engagement with the first groove along a first semiperimeter and folded back to be disposed in engagement with the second groove along the first semiperimeter, and wherein the second wire is disposed in engagement with the second groove along a second semiperimeter and folded back to be disposed in engagement with the first groove along the second semiperimeter.

7. The X-ray CT device according to claim 2, wherein the primary part includes an annular primary core having three legs that define a couple of circumferentially extending grooves therebetween to define an E-shaped cross section, the couple of grooves respectively receiving the primary winding defining the first current path and the second current path; and wherein the secondary core includes an outer leg provided along its outer peripheral edge, an inner leg provided along its inner peripheral edge, and a central leg provided between the outer and inner legs, the secondary core having a couple of circumferentially extending grooves to define an E-shaped cross section, and wherein at least a portion of the secondary winding is configured to be received by the couple of grooves defined on the secondary, core and annularly wound around the central leg, and wherein the primary and the secondary cores are configured so that the legs provided at the primary core and the secondary core confront each other.

8. The X-ray CT device according to claim 7, wherein the secondary part includes an insulation panel having a central opening that allows engagement of the central leg of the secondary core, a portion of the insulation panel being received by the grooves of the secondary core, and wherein the insulation panel has a side groove defined all around its perimeter and extending from its peripheral edge to a proximity of the central opening, the side groove being defined by a top panel and a bottom panel, and wherein a middle panel is provided between the top panel and the bottom panel to bisect the side groove, the middle panel being partially notched at its edge to define a recess communicating to a bottom of the side groove, and wherein the secondary winding is wound between the top panel and the middle panel and also wound between the middle panel and the bottom panel through the recess.

9. The X-ray CT device according to claim 8, wherein the insulation panel comprises a stack of the top panel provided with the central opening, the bottom panel having a central opening, the middle panel having a central opening, a first spacer panel having a central opening and residing between the top panel and the middle panel and which outer peripheral face defines the bottom of the side groove, a second spacer panel having a central opening and residing between the middle panel and the bottom panel and which outer peripheral face defines the bottom of the side groove.

10. The X-ray CT device according to claim 8, wherein the insulation panel comprises a resin mold.

11. The X-ray CT device according to claim 8, wherein the insulation panel comprises a plurality of heat sensitive insulating sheets pressed together.

12. The X-ray CT device according to claim 8, wherein the secondary part includes an insulation element that encloses the side groove of the insulation panel containing the secondary winding.

13. A method of manufacturing the X-ray CT device according to claim 8 comprising:
introducing a portion of a wiring constituting the secondary winding into the recess to define a start point of winding,
winding one side of the wiring relative to the start point to be wound in a first winding direction between the top panel and the middle panel so as to expand radially outward from the bottom of the side groove, and
winding other side of the wiring relative to the start point to be wound in a second winding direction opposite the first direction between the middle panel and the bottom panel so as to expand radially outward from the bottom of the side groove.

14. The X-ray CT device according to claim 7, wherein the secondary part includes an insulation element between the outer leg and the inner leg of the secondary core and the secondary winding.

15. The X-ray CT device according to claim 14, wherein the insulation element is provided on a side surface of the outer leg and the inner leg respectively.

16. The X-ray CT device according to claim 15, wherein the secondary core and the insulation element are configured as an integral mold.

17. The X-ray CT device according to claim 1, wherein the secondary cores are circumferentially disposed at constant angular interval.

18. The X-ray CT device according to claim 1, wherein the secondary cores are disposed within a predetermined arch-shaped area.

19. The X-ray CT device according to claim 1, wherein the secondary winding is earthed at its intermediate portion.

* * * * *